United States Patent
Lippert et al.

(10) Patent No.: US 11,452,541 B2
(45) Date of Patent: Sep. 27, 2022

(54) INTRAVASCULAR DEVICE HAVING A SELECTIVELY DEFLECTABLE TIP

(71) Applicant: SCIENTIA VASCULAR, INC., West Valley City, UT (US)

(72) Inventors: John A. Lippert, Park City, UT (US); Edward J. Snyder, Park City, UT (US)

(73) Assignee: SCIENTIA VASCULAR, INC., West Valley City, UT (US)

( * ) Notice: Subject to any disclaimer, the term of this patent is extended or adjusted under 35 U.S.C. 154(b) by 0 days.

(21) Appl. No.: 15/848,878

(22) Filed: Dec. 20, 2017

(65) Prior Publication Data

US 2018/0177517 A1 Jun. 28, 2018

Related U.S. Application Data

(60) Provisional application No. 62/438,407, filed on Dec. 22, 2016.

(51) Int. Cl.
| | |
|---|---|
| *A61B 17/3207* | (2006.01) |
| *A61M 25/01* | (2006.01) |
| *A61M 25/09* | (2006.01) |
| *A61B 17/00* | (2006.01) |
| *A61M 25/00* | (2006.01) |

(52) U.S. Cl.
CPC ..... *A61B 17/3207* (2013.01); *A61M 25/0138* (2013.01); *A61M 25/09* (2013.01); *A61B 2017/00309* (2013.01); *A61B 2017/00867* (2013.01); *A61B 2017/00951* (2013.01); *A61B 2017/320733* (2013.01); *A61M 25/0147* (2013.01); *A61M 2025/0042* (2013.01)

(58) Field of Classification Search
CPC .......... A61B 17/3207; A61M 25/0138; A61M 25/09
USPC .......................................................... 600/585
See application file for complete search history.

(56) References Cited

U.S. PATENT DOCUMENTS

| | | |
|---|---|---|
| 2,022,065 A | 11/1935 | Wappler |
| 2,187,299 A | 1/1940 | Burkhardt |
| 3,183,702 A | 5/1965 | Zittel |

(Continued)

FOREIGN PATENT DOCUMENTS

| | | |
|---|---|---|
| AU | 723040 | 12/1997 |
| AU | 733966 | 5/2001 |

(Continued)

OTHER PUBLICATIONS

U.S. Appl. No. 15/611,344, Mar. 26, 2019, Office Action.

(Continued)

*Primary Examiner* — Daniel L Cerioni
(74) *Attorney, Agent, or Firm* — Workman Nydegger

(57) ABSTRACT

An intravascular device, such as s guidewire device, includes a hollow proximal section and a hollow distal section joined to the proximal section and extending distally from the proximal section to form a continuous lumen extending from a proximal end of the device to a distal end of the device. An inner member extends from the proximal end to the distal end and is joined to the distal end. The inner member is translatable within the lumen in response to applied tension. At least the distal section includes a microfabricated cutting pattern that enables deflection of the distal end in response to the application of tension to the inner member.

16 Claims, 12 Drawing Sheets

(56) References Cited

U.S. PATENT DOCUMENTS

| | | |
|---|---|---|
| 3,572,334 A | 3/1971 | Petterson |
| 3,612,058 A | 10/1971 | Ackerman |
| 3,709,271 A | 1/1973 | Flory |
| 3,920,058 A | 11/1975 | Walker |
| 4,163,406 A | 8/1979 | Crawford |
| 4,239,069 A | 12/1980 | Zimmerman |
| 4,416,312 A | 11/1983 | Ostberg |
| 4,688,540 A | 8/1987 | Ono |
| 4,719,924 A | 1/1988 | Crittenden |
| 4,801,297 A | 1/1989 | Mueller |
| 4,846,186 A | 7/1989 | Box |
| 4,895,168 A | 1/1990 | Machek |
| 4,989,608 A | 2/1991 | Ratner |
| 5,047,045 A | 9/1991 | Arney et al. |
| 5,069,217 A | 12/1991 | Fleischhacker |
| 5,084,022 A | 1/1992 | Claude |
| 5,095,915 A | 3/1992 | Angelson |
| 5,102,390 A | 4/1992 | Crittenden et al. |
| 5,147,317 A | 9/1992 | Shank |
| 5,154,725 A | 10/1992 | Leopold |
| 5,174,302 A | 12/1992 | Palmer |
| 5,315,996 A | 5/1994 | Lundquist |
| 5,326,374 A | 7/1994 | Ilbawi et al. |
| 5,345,945 A | 9/1994 | Hodgson et al. |
| 5,372,587 A | 12/1994 | Hammerslag |
| 5,382,259 A | 1/1995 | Phelps |
| 5,385,152 A | 1/1995 | Abele |
| 5,437,288 A | 8/1995 | Schwartz |
| 5,441,483 A | 8/1995 | Avitall |
| 5,506,682 A | 4/1996 | Pryor |
| 5,507,751 A | 4/1996 | Goode et al. |
| 5,551,444 A | 9/1996 | Finlayson |
| 5,554,114 A | 9/1996 | Wallace et al. |
| 5,569,218 A | 10/1996 | Berg |
| 5,573,520 A | 11/1996 | Schwartz |
| 5,573,867 A | 11/1996 | Zafred et al. |
| 5,659,205 A | 8/1997 | Weisser |
| 5,673,707 A | 10/1997 | Chandrasekaran |
| 5,676,659 A | 10/1997 | McGurk |
| 5,685,868 A | 11/1997 | Lundquist |
| 5,690,120 A | 11/1997 | Jacobsen |
| 5,706,826 A | 1/1998 | Schwager |
| 5,741,429 A | 4/1998 | Donadio |
| 5,746,701 A | 5/1998 | Noone |
| 5,792,154 A | 8/1998 | Doan |
| 5,800,454 A | 9/1998 | Jacobsen |
| 5,833,631 A | 11/1998 | Nguyen |
| 5,833,632 A | 11/1998 | Jacobsen |
| 5,842,461 A | 12/1998 | Azuma |
| 5,860,963 A | 1/1999 | Azam et al. |
| 5,876,356 A | 3/1999 | Viera et al. |
| 5,911,715 A | 6/1999 | Berg |
| 5,911,717 A | 6/1999 | Jacobsen |
| 5,916,194 A | 6/1999 | Jacobsen |
| 5,931,830 A | 8/1999 | Jacobsen |
| 5,954,672 A | 9/1999 | Schwager |
| 6,004,279 A | 12/1999 | Crowley |
| 6,014,919 A | 1/2000 | Jacobsen |
| 6,017,319 A | 1/2000 | Jacobsen |
| 6,022,343 A | 2/2000 | Johnson et al. |
| 6,022,369 A | 2/2000 | Jacobsen |
| 6,027,863 A | 2/2000 | Donadis |
| 6,033,288 A | 3/2000 | Weisshaus |
| 6,033,394 A | 3/2000 | Vidlund |
| 6,056,702 A | 5/2000 | Lorenzo |
| 6,063,101 A | 5/2000 | Jacobsen |
| 6,110,164 A | 8/2000 | Vidlund |
| 6,132,389 A | 10/2000 | Cornish |
| 6,139,511 A | 10/2000 | Huter |
| 6,168,570 B1 | 1/2001 | Ferrera |
| 6,179,828 B1 | 1/2001 | Mottola |
| 6,183,410 B1 | 2/2001 | Jacobsen |
| 6,183,420 B1 | 2/2001 | Douk et al. |
| 6,214,042 B1 | 4/2001 | Jacobsen |
| 6,228,073 B1 | 5/2001 | Noone |
| 6,245,030 B1 | 6/2001 | Dubois |
| 6,251,086 B1 | 6/2001 | Cornelius |
| 6,260,458 B1 | 7/2001 | Jacobsen |
| 6,261,246 B1 | 7/2001 | Pantages et al. |
| 6,273,881 B1 | 8/2001 | Kiemeneij |
| 6,302,870 B1 | 10/2001 | Jacobsen |
| 6,306,105 B1 | 10/2001 | Rooney |
| 6,346,091 B1 | 2/2002 | Jacobsen |
| 6,356,791 B1 | 3/2002 | Westlund |
| 6,402,706 B2 | 6/2002 | Richardson et al. |
| 6,428,489 B1 | 8/2002 | Jacobsen |
| 6,431,039 B1 | 8/2002 | Jacobsen |
| 6,436,056 B1 | 8/2002 | Wang et al. |
| 6,440,088 B1 | 8/2002 | Jacobsen |
| 6,458,867 B1 | 10/2002 | Wang |
| 6,464,651 B1 | 10/2002 | Hiejima et al. |
| 6,492,615 B1 | 12/2002 | Flanagan |
| 6,494,894 B2 | 12/2002 | Mirarchi |
| 6,527,732 B1 | 3/2003 | Strauss |
| 6,527,746 B1 | 3/2003 | Oslund |
| 6,553,880 B2 | 4/2003 | Jacobsen |
| 6,554,820 B1 | 4/2003 | Wendlandt |
| 6,558,355 B1 | 5/2003 | Metzger |
| 6,579,246 B2 | 6/2003 | Jacobsen |
| 6,602,207 B1 | 8/2003 | Mam |
| 6,606,985 B2 | 8/2003 | Negishi |
| 6,610,046 B1 | 8/2003 | Usami et al. |
| 6,627,724 B2 | 9/2003 | Meijs et al. |
| 6,652,508 B2 | 11/2003 | Griffin |
| 6,671,560 B2 | 12/2003 | Westlund |
| 6,766,720 B1 | 7/2004 | Jacobsen |
| 6,805,676 B2 | 10/2004 | Klint |
| RE39,018 E | 3/2006 | Azuma |
| 7,024,885 B2 | 4/2006 | Villalobos |
| 7,097,624 B2 | 8/2006 | Campion |
| 7,110,910 B1 | 9/2006 | Deffenbaugh et al. |
| 7,128,718 B2 | 10/2006 | Hojeibane et al. |
| 7,182,735 B2 | 2/2007 | Shireman |
| 7,276,062 B2 | 10/2007 | McDaniel et al. |
| 7,338,345 B2 | 3/2008 | Fujinami |
| 7,421,929 B2 | 9/2008 | French |
| 7,494,474 B2 | 2/2009 | Richardson et al. |
| 7,507,246 B2 | 3/2009 | McGuckin et al. |
| 7,621,880 B2 | 11/2009 | Ryan |
| 7,637,875 B2 | 12/2009 | Itou |
| 7,641,622 B2 | 1/2010 | Satou |
| 7,670,302 B2 | 3/2010 | Griffin |
| 7,699,792 B2 | 4/2010 | Hofmann |
| 7,722,545 B2 | 5/2010 | Bertsch |
| 7,722,552 B2 | 5/2010 | Aimi |
| 7,744,545 B2 | 6/2010 | Aimi |
| 7,747,314 B2 | 6/2010 | Parins |
| 7,753,859 B2 | 7/2010 | Kinoshita |
| 7,766,896 B2 | 8/2010 | Volk |
| 7,769,839 B2 | 8/2010 | Boivie et al. |
| 7,785,273 B2 | 8/2010 | Eskuri |
| 7,789,839 B2 | 9/2010 | Lupton |
| 7,806,837 B2 | 10/2010 | Rasmussen |
| 7,878,984 B2 | 2/2011 | Jacobsen |
| 7,883,474 B1 | 2/2011 | Mirigian |
| 7,914,467 B2 | 3/2011 | Layman et al. |
| 7,942,832 B2 | 5/2011 | Kanuka |
| 7,989,042 B2 | 8/2011 | Obara et al. |
| 8,043,314 B2 | 10/2011 | Noriega et al. |
| 8,048,004 B2 | 11/2011 | Davis et al. |
| 8,105,246 B2 | 1/2012 | Voeller |
| 8,128,579 B2 | 3/2012 | Chen |
| 8,128,580 B2 | 3/2012 | Fujimagari |
| 8,137,293 B2 | 3/2012 | Zhou |
| 8,167,821 B2 | 5/2012 | Sharrow et al. |
| 8,257,279 B2 | 9/2012 | Jacobsen |
| 8,292,828 B2 | 10/2012 | Uihlein |
| 8,357,140 B2 | 1/2013 | Majercak |
| 8,376,961 B2 | 2/2013 | Layman |
| 8,377,056 B2 | 2/2013 | Oyola et al. |
| 8,409,114 B2 | 4/2013 | Parins |
| 8,409,169 B1 | 4/2013 | Moss |
| 8,444,577 B2 | 5/2013 | Bunch |
| 8,454,535 B2 | 6/2013 | Majercak |

(56) References Cited

U.S. PATENT DOCUMENTS

| | | |
|---|---|---|
| 8,460,213 B2 | 6/2013 | Northrop |
| 8,468,919 B2 | 6/2013 | Christian |
| 8,500,658 B2 | 8/2013 | Boyle |
| 8,517,959 B2 | 8/2013 | Kurosawa |
| 8,535,243 B2 | 9/2013 | Shireman |
| 8,540,648 B2 | 9/2013 | Uihlein |
| 8,551,020 B2 | 10/2013 | Chen |
| 8,551,021 B2 | 10/2013 | Voeller |
| 8,622,931 B2 | 1/2014 | Teague |
| 8,622,933 B2 | 1/2014 | Maki |
| 8,728,075 B2 | 5/2014 | Wu et al. |
| 8,758,269 B2 | 6/2014 | Miyata et al. |
| 8,795,202 B2 | 8/2014 | Northrop |
| 8,795,254 B2 | 8/2014 | Layman |
| 8,821,477 B2 | 9/2014 | Northrop |
| 8,870,790 B2 | 10/2014 | Jacobsen |
| 8,900,163 B2 | 12/2014 | Jacobsen |
| 8,915,865 B2 | 12/2014 | Jacobsen et al. |
| 8,932,235 B2 | 1/2015 | Jacobsen |
| 8,936,558 B2 | 1/2015 | Jacobsen |
| 8,939,916 B2 | 1/2015 | Jacobsen |
| 8,956,310 B2 | 2/2015 | Miyata |
| 9,067,332 B2 | 6/2015 | Lippert |
| 9,067,333 B2 | 6/2015 | Lippert |
| 9,072,873 B2 | 7/2015 | Lippert |
| 9,072,874 B2 | 7/2015 | Northrop |
| 9,364,589 B2 | 6/2016 | Cage |
| 9,550,013 B2 | 1/2017 | Kawasaki |
| 9,616,195 B2 | 4/2017 | Lippert |
| 9,623,212 B2 | 4/2017 | Tano |
| 9,662,798 B2 | 5/2017 | Christian |
| 9,700,702 B2 | 7/2017 | Tano |
| 9,848,882 B2 | 12/2017 | Lippert |
| 9,950,137 B2 | 4/2018 | Lippert |
| 10,252,024 B2 | 4/2019 | Northrop |
| 10,363,389 B2 | 7/2019 | Lippert et al. |
| 10,639,456 B2 | 5/2020 | Peralta |
| 2001/0009980 A1 | 7/2001 | Richardson et al. |
| 2002/0013540 A1 | 1/2002 | Jacobsen et al. |
| 2002/0019599 A1 | 2/2002 | Rooney |
| 2002/0049392 A1 | 4/2002 | DeMello |
| 2002/0062524 A1 | 5/2002 | Vogland et al. |
| 2002/0078808 A1 | 6/2002 | Jacobsen et al. |
| 2002/0082624 A1 | 6/2002 | Anderson |
| 2003/0009208 A1 | 1/2003 | Snyder et al. |
| 2003/0023190 A1 | 1/2003 | Cox |
| 2003/0069521 A1 | 4/2003 | Reynolds et al. |
| 2003/0069522 A1* | 4/2003 | Jacobsen ............ A61M 25/0013 600/585 |
| 2003/0093059 A1 | 5/2003 | Griffin et al. |
| 2003/0119869 A1 | 6/2003 | Burrows et al. |
| 2003/0125641 A1 | 7/2003 | Jafari et al. |
| 2004/0039371 A1 | 2/2004 | Tockman et al. |
| 2004/0054349 A1 | 3/2004 | Brightbill |
| 2004/0087933 A1 | 5/2004 | Lee |
| 2004/0093060 A1 | 5/2004 | Seguin et al. |
| 2004/0102719 A1 | 5/2004 | Keith et al. |
| 2004/0102720 A1 | 5/2004 | Kellerman et al. |
| 2004/0111044 A1 | 6/2004 | Davis et al. |
| 2004/0122340 A1 | 6/2004 | Vrba et al. |
| 2004/0167440 A1 | 8/2004 | Sharrow et al. |
| 2004/0181174 A2 | 9/2004 | Davis |
| 2004/0186485 A1 | 9/2004 | Kear |
| 2004/0193140 A1 | 9/2004 | Griffin |
| 2004/0225292 A1 | 11/2004 | Sasso et al. |
| 2004/0254450 A1 | 12/2004 | Griffin et al. |
| 2005/0054953 A1 | 3/2005 | Ryan |
| 2005/0124976 A1 | 6/2005 | Devens, Jr. et al. |
| 2005/0274384 A1 | 12/2005 | Tran et al. |
| 2006/0041186 A1 | 2/2006 | Vancalllie |
| 2006/0074442 A1* | 4/2006 | Noriega ............ A61B 17/32002 606/159 |
| 2006/0089618 A1 | 4/2006 | McFerran |
| 2006/0112802 A1 | 6/2006 | Fujinami |
| 2006/0121218 A1 | 6/2006 | Obara et al. |
| 2006/0189896 A1 | 8/2006 | Davis et al. |
| 2006/0216049 A1 | 9/2006 | Julien et al. |
| 2006/0241519 A1 | 10/2006 | Hojeibane et al. |
| 2006/0262474 A1 | 11/2006 | Chen et al. |
| 2007/0010786 A1 | 1/2007 | Casey et al. |
| 2007/0100285 A1 | 5/2007 | Griffin |
| 2007/0112331 A1 | 5/2007 | Weber et al. |
| 2007/0135763 A1 | 6/2007 | Musbach |
| 2007/0142893 A1 | 6/2007 | Buiser et al. |
| 2007/0167876 A1 | 7/2007 | Euteneuer et al. |
| 2007/0185415 A1 | 8/2007 | Ressemann et al. |
| 2007/0221230 A1 | 9/2007 | Thompson |
| 2007/0233039 A1* | 10/2007 | Mitelberg ............ A61M 25/09 604/523 |
| 2007/0250036 A1 | 10/2007 | Volk |
| 2007/0287955 A1 | 12/2007 | Layman et al. |
| 2008/0021347 A1 | 1/2008 | Jacobsen et al. |
| 2008/0021401 A1 | 1/2008 | Jacobsen et al. |
| 2008/0021404 A1 | 1/2008 | Jacobsen et al. |
| 2008/0064989 A1 | 3/2008 | Chen et al. |
| 2008/0077049 A1 | 3/2008 | Hirshman |
| 2008/0086854 A1 | 4/2008 | Boyd |
| 2008/0097246 A1 | 4/2008 | Stafford |
| 2008/0097247 A1 | 4/2008 | Eskuri |
| 2008/0097248 A1 | 4/2008 | Munoz |
| 2008/0122226 A1 | 5/2008 | Madison |
| 2008/0125674 A1 | 5/2008 | Bilecen et al. |
| 2008/0147170 A1 | 6/2008 | Vrba |
| 2008/0188298 A1 | 8/2008 | Seelig et al. |
| 2008/0188928 A1* | 8/2008 | Salahieh ............ A61M 25/0662 623/2.11 |
| 2008/0200839 A1 | 8/2008 | Bunch et al. |
| 2008/0262474 A1 | 10/2008 | Northrop |
| 2008/0269641 A1 | 10/2008 | O'Shaughnessy et al. |
| 2008/0319525 A1 | 12/2008 | Tieu |
| 2009/0036832 A1 | 2/2009 | Skujins et al. |
| 2009/0036833 A1 | 2/2009 | Parins |
| 2009/0043283 A1 | 2/2009 | Tumnlund et al. |
| 2009/0043372 A1 | 2/2009 | Northrop et al. |
| 2009/0118675 A1 | 5/2009 | Czyscon et al. |
| 2009/0177119 A1 | 7/2009 | Heidner |
| 2009/0177185 A1 | 7/2009 | Northrop |
| 2009/0254000 A1 | 10/2009 | Layman et al. |
| 2009/0292225 A1 | 11/2009 | Chen et al. |
| 2009/0318892 A1 | 12/2009 | Aboytes et al. |
| 2010/0063479 A1 | 3/2010 | Merdan |
| 2010/0114017 A1 | 5/2010 | Lenker et al. |
| 2010/0114302 A1 | 5/2010 | Tzafrir et al. |
| 2010/0139465 A1 | 6/2010 | Christian et al. |
| 2010/0228150 A1* | 9/2010 | Zimmerman ............ A61M 25/09 600/585 |
| 2010/0256527 A1 | 10/2010 | Lippert et al. |
| 2010/0256528 A1 | 10/2010 | Lippert |
| 2010/0256601 A1 | 10/2010 | Lippert et al. |
| 2010/0256602 A1 | 10/2010 | Lippert et al. |
| 2010/0256603 A1 | 10/2010 | Lippert |
| 2010/0256604 A1 | 10/2010 | Lippert |
| 2010/0256605 A1 | 10/2010 | Lippert et al. |
| 2010/0256606 A1 | 10/2010 | Lippert et al. |
| 2010/0318066 A1 | 12/2010 | Miyata et al. |
| 2011/0011226 A1 | 1/2011 | Tsurusawa |
| 2011/0022003 A1 | 1/2011 | Tekulve |
| 2011/0160680 A1 | 6/2011 | Cage et al. |
| 2011/0245807 A1 | 10/2011 | Sakata et al. |
| 2011/0245808 A1 | 10/2011 | Voeller et al. |
| 2011/0251519 A1 | 10/2011 | Romoscanu |
| 2012/0065623 A1 | 3/2012 | Nelson, III |
| 2012/0168034 A1 | 6/2012 | Wilson |
| 2012/0209073 A1 | 8/2012 | McWeeney et al. |
| 2012/0239074 A1 | 9/2012 | Aboytes et al. |
| 2012/0271397 A1 | 10/2012 | Muzslay et al. |
| 2012/0289938 A1 | 11/2012 | Northrop et al. |
| 2013/0018359 A1 | 1/2013 | Coyle |
| 2013/0096553 A1 | 4/2013 | Hill et al. |
| 2013/0110000 A1 | 5/2013 | Tully |
| 2013/0226033 A1 | 8/2013 | Eskuri |
| 2013/0255456 A1 | 10/2013 | Christian |
| 2014/0094787 A1 | 4/2014 | Reynolds |
| 2014/0187983 A1 | 7/2014 | Anderson |

(56) References Cited

U.S. PATENT DOCUMENTS

| | | |
|---|---|---|
| 2014/0257363 A1 | 9/2014 | Lippert |
| 2014/0276109 A1 | 9/2014 | Gregorich |
| 2014/0276787 A1 | 9/2014 | Wang et al. |
| 2014/0309657 A1 | 10/2014 | Ben-Ami |
| 2014/0336620 A1 | 11/2014 | Layman et al. |
| 2015/0011834 A1 | 1/2015 | Ayala et al. |
| 2015/0011964 A1 | 1/2015 | Abner |
| 2015/0190614 A1 | 7/2015 | Uihlein |
| 2015/0216533 A1 | 8/2015 | Gray et al. |
| 2015/0238734 A1 | 8/2015 | Kanazawa |
| 2015/0290432 A1 | 10/2015 | Mathews |
| 2015/0297863 A1 | 10/2015 | Hannon et al. |
| 2015/0305710 A1 | 10/2015 | Koninklijke |
| 2015/0306355 A1 | 10/2015 | Idstrom |
| 2016/0008585 A1 | 1/2016 | Tano |
| 2016/0045101 A1* | 2/2016 | Nakatate ............. A61B 5/6851 600/478 |
| 2016/0089128 A1 | 3/2016 | Weber et al. |
| 2016/0113793 A1 | 4/2016 | Nishigishi |
| 2016/0135827 A1 | 5/2016 | Elsesser |
| 2016/0199620 A1 | 7/2016 | Pokorney |
| 2016/0235337 A1 | 8/2016 | Govari |
| 2016/0361520 A1 | 12/2016 | Braun |
| 2016/0367788 A1 | 12/2016 | Jimenez et al. |
| 2016/0375226 A1 | 12/2016 | Nabeshima |
| 2017/0047740 A1 | 2/2017 | Narla |
| 2017/0189643 A1 | 7/2017 | Christian |
| 2017/0203076 A1 | 7/2017 | Groneberg et al. |
| 2017/0281909 A1 | 10/2017 | Northrop et al. |
| 2018/0015261 A1 | 1/2018 | Lippert |
| 2018/0015262 A1 | 1/2018 | Lippert |
| 2018/0015263 A1 | 1/2018 | Lippert |
| 2018/0028177 A1 | 2/2018 | Van et al. |
| 2018/0071496 A1 | 3/2018 | Snyder |
| 2018/0185619 A1 | 7/2018 | Batman et al. |
| 2018/0193607 A1 | 7/2018 | Lippert et al. |
| 2018/0207407 A1 | 7/2018 | Tanigaki |
| 2019/0105463 A1 | 4/2019 | Christian et al. |
| 2019/0255290 A1 | 8/2019 | Snyder et al. |
| 2019/0290883 A1 | 9/2019 | Lippert et al. |
| 2020/0054860 A1 | 2/2020 | McElhaney et al. |
| 2020/0094027 A1 | 3/2020 | Davis |
| 2020/0121308 A1 | 4/2020 | Davis et al. |
| 2020/0222672 A1 | 7/2020 | Davis et al. |
| 2020/0345975 A1 | 11/2020 | Snyder |
| 2021/0162184 A1 | 6/2021 | Lippert et al. |
| 2021/0178128 A1 | 6/2021 | Lippert et al. |
| 2021/0213241 A1 | 7/2021 | Christian et al. |
| 2021/0228845 A1 | 7/2021 | Lippert et al. |
| 2021/0283380 A1 | 9/2021 | Lippert et al. |
| 2021/0346656 A1 | 11/2021 | Lippert et al. |

FOREIGN PATENT DOCUMENTS

| | | |
|---|---|---|
| AU | 774559 | 7/2004 |
| AU | 2008229892 | 10/2008 |
| BR | 9709363 | 1/2000 |
| BR | 9712829 | 1/2000 |
| CA | 2266685 | 5/2006 |
| CA | 2255781 | 3/2007 |
| CA | 2395149 | 12/2008 |
| CN | 1230914 | 10/1999 |
| CN | 1324285 | 11/2001 |
| CN | 1422673 | 6/2003 |
| CN | 1518428 | 8/2004 |
| CN | 1781684 | 6/2006 |
| CN | 1897892 A | 1/2007 |
| CN | 101001660 | 7/2007 |
| CN | 101209365 A | 7/2008 |
| CN | 101304778 | 11/2008 |
| CN | 201239164 Y | 5/2009 |
| CN | 101815553 A | 8/2010 |
| CN | 102049085 A | 5/2011 |
| CN | 102107041 A | 6/2011 |
| CN | 102824681 A | 12/2012 |
| CN | 102847225 A | 1/2013 |
| CN | 103764012 A | 4/2014 |
| CN | 103860265 A | 6/2014 |
| CN | 104271035 A | 1/2015 |
| CN | 104602616 A | 5/2015 |
| CN | 105209102 A | 12/2015 |
| CN | 105545375 A | 5/2016 |
| CN | 105682729 A | 6/2016 |
| CN | 105828690 A | 8/2016 |
| CN | 105979880 A | 9/2016 |
| DE | 60036882 | 7/2008 |
| DE | 69738235 | 7/2008 |
| EP | 0521595 A2 | 1/1993 |
| EP | 0998323 A1 | 5/2000 |
| EP | 934141 | 11/2005 |
| EP | 921754 | 10/2007 |
| EP | 1239901 | 10/2007 |
| EP | 1940498 | 7/2008 |
| EP | 2964305 | 1/2016 |
| ES | 2293660 | 3/2008 |
| JP | 59102509 | 6/1984 |
| JP | 06-154335 A | 6/1994 |
| JP | 07-008560 | 1/1995 |
| JP | 08-308934 | 11/1996 |
| JP | 11294497 | 10/1999 |
| JP | 2000116787 | 4/2000 |
| JP | 2000511094 | 8/2000 |
| JP | 2000343313 | 12/2000 |
| JP | 2001500808 | 1/2001 |
| JP | 2002543896 | 12/2002 |
| JP | 2003011117 | 1/2003 |
| JP | 2004-025340 A | 1/2004 |
| JP | 2004136121 | 5/2004 |
| JP | 2004329552 | 11/2004 |
| JP | 2004535233 | 11/2004 |
| JP | 2005-514115 A | 5/2005 |
| JP | 2005-534407 A | 11/2005 |
| JP | 2005533594 | 11/2005 |
| JP | 2007313638 | 12/2007 |
| JP | 2008536639 | 9/2008 |
| JP | 2010-029736 A | 2/2010 |
| JP | 2010-503484 A | 2/2010 |
| JP | 2010-535583 A | 11/2010 |
| JP | 2010535588 | 11/2010 |
| JP | 2011-206175 A | 10/2011 |
| JP | 4805208 | 11/2011 |
| JP | 4845313 | 12/2011 |
| JP | 2013-523282 A | 6/2013 |
| JP | 2015-181723 A | 10/2015 |
| JP | 2015-186427 A | 10/2015 |
| JP | 2017-169253 A | 9/2017 |
| KR | 20000015896 | 3/2000 |
| KR | 20000036139 | 6/2000 |
| TW | 412468 | 11/2000 |
| WO | 9419039 | 1/1994 |
| WO | 1994006503 | 3/1994 |
| WO | 98/58697 A1 | 12/1998 |
| WO | 99/04847 A1 | 2/1999 |
| WO | 9953824 | 10/1999 |
| WO | 2004011076 | 2/2004 |
| WO | 2006/025931 A1 | 3/2006 |
| WO | 2006/058234 A2 | 6/2006 |
| WO | 2006113863 | 10/2006 |
| WO | 2007050718 | 5/2007 |
| WO | 2008/034010 A2 | 3/2008 |
| WO | 2009/020691 A2 | 2/2009 |
| WO | 2009/020836 A1 | 2/2009 |
| WO | 2009020961 | 2/2009 |
| WO | 2009020962 | 2/2009 |
| WO | 2010077692 | 7/2010 |
| WO | 2010115163 | 10/2010 |
| WO | 2011/123689 A1 | 10/2011 |
| WO | 2014/005095 A1 | 1/2014 |
| WO | 2014066104 | 5/2014 |
| WO | 2014138580 | 9/2014 |
| WO | 2016047499 | 3/2016 |
| WO | 2016117238 | 7/2016 |
| WO | 2016136609 | 9/2016 |

(56) References Cited

FOREIGN PATENT DOCUMENTS

| WO | 2016152194 |    | 9/2016  |
|----|------------|----|---------|
| WO | 2016158671 |    | 10/2016 |
| WO | 2018/017349| A1 | 1/2018  |
| WO | 2018218216 |    | 11/2018 |
| WO | 2020/217171|    | 10/2020 |

OTHER PUBLICATIONS

U.S. Appl. No. 15/698,553, Nov. 27, 2019, Office Action.
U.S. Appl. No. 15/917,255, filed Mar. 9, 2018, Lippert.
Canadian Office Action for CA2767655 dated Jan. 2, 2018.
EP10759515.9 Supplementary European Search Report dated Sep. 25, 2012.
European Search Report for EP09836735 dated Nov. 7, 2012.
Supplementary Partial European Search Report for EP14760849 dated Oct. 11, 2016.
European Search Report for EP15197042.3 dated Apr. 11, 2016.
European Search Report for application No. 17184064.8 dated Jan. 5, 2018.
International Search Report and Written Opinion for PCT/US2009/067217 dated Dec. 16, 2010.
International Search Report and Written Opinion for PCT/US2010/029567 dated Jun. 1, 2010.
International Search Report and Written Opinion for PCT/US2014/021742 dated Aug. 27, 2014.
International Search Report and Written Opinion for PCT/US2017/041299 dated Oct. 2, 2017.
International Search Report and Written Opinion for PCT/US2017/041301 dated Oct. 2, 2017.
International Search Report and Written Opinion for PCT/US2017/041305 dated Oct. 2, 2017.
International Search Report and Written Opinion for application PCT/US20171050802 dated Nov. 7, 2017.
International Search Report and Written Opinion for PCT/US2018/034723 dated Sep. 5, 2018.
International Search Report and Written Opinion for PCT/US2018/034756 dated Aug. 14, 2018.
U.S. Appl. No. 12/633,727, Oct. 16, 2012, Office Action.
U.S. Appl. No. 12/633,727, Feb. 28, 2013, Notice of Allowance.
U.S. Appl. No. 12/753,831, Feb. 1, 2012, Office Action.
U.S. Appl. No. 12/75,3831, May 31, 2012, Final Office Action.
U.S. Appl. No. 12/753,831, Mar. 21, 2014, Office Action.
U.S. Appl. No. 12/753,831, Aug. 29, 2014, Final Office Action.
U.S. Appl. No. 12/753,831, Apr. 14, 2015, Notice of Allowance.
U.S. Appl. No. 12/753,836, Dec. 9, 2011, Office Action.
U.S. Appl. No. 12/753,836, May 1, 2012, Final Office Action.
U.S. Appl. No. 12/753,838, Jul. 31, 2014, Office Action.
U.S. Appl. No. 12/753,836, Jan. 9, 2015, Final Office Action.
U.S. Appl. No. 12/753,838, Jun. 26, 2015, Office Action.
U.S. Appl. No. 12/753,836, Feb. 17, 2016, Final Office Action.
U.S. Appl. No. 12/753,836, Dec. 23, 2016, Office Action.
U.S. Appl. No. 12/753,636, Jul. 14, 2017, Final Office Action.
U.S. Appl. No. 12/753,836, Nov. 24, 2017, Notice of Allowance.
U.S. Appl. No. 12/753,839, Feb. 7, 2012, Office Action.
U.S. Appl. No. 12/753,839, May 31, 2012, Final Office Action.
U.S. Appl. No. 12/753,839, May 5, 2014, Office Action.
U.S. Appl. No. 12/753,842, Aug. 1, 2012, Office Action.
U.S. Appl. No. 12/753,842, Jan. 9, 2013, Final Office Action.
U.S. Appl. No. 12/753,842, Jan. 29, 2014, Office Action.
U.S. Appl. No. 12/753,842, Sep. 4, 2014, Final Office Action.
U.S. Appl. No. 12/753,842, Dec. 29, 2014, Notice of Allowance.
U.S. Appl. No. 12/753,842, Mar. 5, 2015, Notice of Allowance.
U.S. Appl. No. 12/753,849, May 10, 2011, Office Action.
U.S. Appl. No. 12/753,849, Oct. 18, 2011, Office Action.
U.S. Appl. No. 12/753,849, Jun. 6, 2012, Final Office Action.
U.S. Appl. No. 12/753,849, Jan. 3, 2013, Office Action.
U.S. Appl. No. 12/753,849, Oct. 9, 2013, Final Office Action.
U.S. Appl. No. 12/753,849, May 27, 2014, Office Action.
U.S. Appl. No. 12/753,849, Nov. 5, 2014, Interview Summary.
U.S. Appl. No. 12/753,849, Feb. 2, 2015, Notice of Allowance.
U.S. Appl. No. 12/753,849, Apr. 30, 2015, Notice of Allowance.
U.S. Appl. No. 12/753,855, Sep. 15, 2011, Office Action.
U.S. Appl. No. 12/753,855, Apr. 18, 2012, Final Office Action.
U.S. Appl. No. 12/753,855, Feb. 28, 2014, Office Action.
U.S. Appl. No. 12/753,855, Jan. 13, 2015, Final Office Action.
U.S. Appl. No. 12/753,855, May 21, 2015, Office Action.
U.S. Appl. No. 12/753,855, May 5, 2016, Office Action.
U.S. Appl. No. 12/753,855, Nov. 30, 2016, Notice of Allowance.
U.S. Appl. No. 12/753,858, May 10, 2011, Office Action.
U.S. Appl. No. 12/753,858, Oct. 19, 2011, Final Office Action.
U.S. Appl. No. 12/753,858, Feb. 3, 2012, Office Action.
U.S. Appl. No. 12/753,858, Jul. 18, 2012, Final Office Action.
U.S. Appl. No. 12/753,858, Mar. 29, 2013, Office Action.
U.S. Appl. No. 12/753,858, Jan. 17, 2014, Final Office Action.
U.S. Appl. No. 12/753,858, Sep. 4, 2014, Office Action.
U.S. Appl. No. 12/753,858, Nov. 4, 2014, Interview Summary.
U.S. Appl. No. 12/753,858, May 28, 2015, Final Office Action.
U.S. Appl. No. 12/753,858, Dec. 30, 2015, Office Action.
U.S. Appl. No. 12/753,858, Oct. 24, 2016, Office Action.
U.S. Appl. No. 12/753,858, Mar. 27, 2017, Office Action.
U.S. Appl. No. 12/753,858, Oct. 20, 2017, Final Office Action.
U.S. Appl. No. 12/753,858, Mar. 13, 2018, Office Action.
U.S. Appl. No. 13/901,375, Dec. 10, 2015, Office Action.
U.S. Appl. No. 13/901,375, Aug. 1, 2016, Office Action.
U.S. Appl. No. 13/901,375, Dec. 27, 2016, Notice of Allowance.
U.S. Appl. No. 14/199,675, Nov. 3, 2016, Office Action.
U.S. Appl. No. 14/199,675, May 18, 2017, Final Office Action.
U.S. Appl. No. 14/199,675, Sep. 6, 2017, Notice of Allowance.
U.S. Appl. No. 15/465,399, Apr. 23, 2018, Office Action.
U.S. Appl. No. 15/611,344, Nov. 12, 2019, Final Office Action.
U.S. Appl. No. 12/753,858, Mar. 14, 2019, Notice of Allowance.
U.S. Appl. No. 15/465,399, Sep. 10, 2018, Notice of Allowance.
International Search Report and Written Opinion for PCT/US2019/019046 dated May 17, 2019.
U.S. Appl. No. 16/281,046, filed Feb. 20, 2019, Snyder.
U.S. Appl. No. 16/439,894, filed Jun. 13, 2019, Lippert.
U.S. Appl. No. 15/606,607 May 14, 2019, Office Action.
U.S. Appl. No. 15/606,607, Nov. 19, 2019, Final Office Action.
U.S. Appl. No. 15/611,328, Mar. 27, 2019, Office Action.
U.S. Appl. No. 16/212,425, filed Dec. 6, 2018, Christian.
International Search Report and Written Opinion for PCT/US2019/021031 dated Jun. 18, 2019.
U.S. Appl. No. 12/753,858, Nov. 14, 2018, Final Office Action.
International Search Report and Written Opinion for PCT/US2017/068056 dated Feb. 26, 2018.
U.S. Appl. No. 15/611,328, Sep. 24, 2019, Final Office Action.
U.S. Appl. No. 15/698,553, May 15, 2020, Notice of Allowance.
U.S. Appl. No. 15/611,344, May 21, 2020, Office Action.
U.S. Appl. No. 16/212,425, Mar. 16, 2020, Office Action.
International Search Report and Written Opinion for Application PCT/US2017/050602 dated Nov. 7, 2017.
International Search Report and Written Opinion received for PCT Patent Application No. PCT/US2020/030589, dated Jul. 17, 2020, 7 pages.
International Search Report and Written Opinion, PCT App. No. PCT/US2020/013754, dated Jun. 9, 2020, 11 pages.
Non-Final Office Action received for U.S. Appl. No. 15/606,607, dated Jun. 10, 2020, 26 pages.
Final Office Action received for U.S. Appl. No. 16/281,046, dated May 11, 2021, 18 pages.
International Search Report and Written Opinion received for PCT Patent Application No. PCT/US21/14656, dated Apr. 28, 2021, 8 pages.
Final Office Action received for U.S. Appl. No. 16/212,425, dated Aug. 3, 2020, 14 pages.
Final Rejection received for U.S. Appl. No. 15/606,607, dated Dec. 15, 2020, 24 pages.
Non-Final Office Action received for U.S. Appl. No. 15/611,328, dated Jun. 29, 2020, 13 pages.
Non-Final Office Action received for U.S. Appl. No. 15/917,255, dated Aug. 17, 2020, 12 pages.

(56) References Cited

OTHER PUBLICATIONS

Non-Final Office Action received for U.S. Appl. No. 16/281,046, dated Oct. 29, 2020, 18 pages.
Notice of Allowance received for U.S. Appl. No. 16/212,425, dated Dec. 23, 2020, 12 pages.
Notice of Allowance received for U.S. Appl. No. 16/212,425, dated Jan. 25, 2021, 2 pages.
U.S. Patent Application filed Jan. 14, 2020, by Clark C. Davis et al., U.S. Appl. No. 16/742,211.
Non-Final Office Action received for U.S. Appl. No. 16/855,366, dated Jun. 23, 2021, 15 pages.
Non-Final Office Action received for U.S. Appl. No. 16/616,139, dated Oct. 26, 2021, 11 pages.
International Preliminary Report on Patentability received for PCT Patent Application No. PCT/US2020/030589, dated Nov. 11, 2021, 7 pages.
International Search Report and Written Opinion received for PCT Patent Application No. PCT/US21/042753, dated Nov. 5, 2021, 14 pages.
Non-Final Office Action received for U.S. Appl. No. 16/855,366, dated Jul. 11, 2022, 13 pages.

\* cited by examiner

INTRAVASCULAR DEVICE HAVING A SELECTIVELY DEFLECTABLE TIP

CROSS-REFERENCE TO RELATED APPLICATIONS

This application claims priority to and the benefit of U.S. Provisional Patent Application Ser. No. 62/438,407, filed on Dec. 22, 2016 and titled "Steerable Intravascular Devices," the entirety of which is incorporated herein by this reference.

BACKGROUND

Interventional devices such as guidewires and catheters are frequently utilized in the medical field to perform delicate procedures deep within the human body. Typically, a catheter is inserted into a patient's femoral, radial, carotid, or jugular vessel and navigated through the patient's vasculature to the heart, brain, or other targeted anatomy as required. Often, a guidewire is first routed to the targeted anatomy, and one or more catheters are subsequently passed over the guidewire and routed to the targeted anatomy. Once in place, the catheter can be used to deliver drugs, stents, embolic devices, radiopaque dyes, or other devices or substances for treating the patient in a desired manner. In other circumstances, a micro catheter and guidewire are routed simultaneously toward the targeted anatomy while the guidewire resides within the micro catheter, and then the guidewire is passed further into the anatomy by translating within the micro catheter.

In many applications, such intravascular devices must be angled through the tortuous bends and curves of a vasculature passageway to arrive at the targeted anatomy. Such an interventional device requires sufficient flexibility, particularly closer to its distal end, to navigate such tortuous pathways. However, other design aspects must also be considered. For example, the interventional device must also be able to provide sufficient torquability (i.e., the ability to transmit torque applied at the proximal end all the way to the distal end), pushability (i.e., the ability to transmit axial push to the distal end rather than bending and binding intermediate portions), and structural integrity for performing intended medical functions.

Many intravascular procedures involve directing an intravascular device to portions of the neurovasculature. These procedures require that the device be guided through the carotid siphon and other tortuous paths. Such maneuvering can be difficult. In some instances, procedures are unable to complete or become much costlier and lengthy because of these difficulties. Precise control of the device is required. However, due to the inherent structure of the vascular anatomy involved, it can be difficult to get the catheter properly positioned at the targeted treatment site.

In some circumstances, it may be necessary to pass the distal tip of the device through a fusiform aneurysm, which can present even further difficulties. When passing the device through normal vasculature, the vascular walls will generally confine the path forward and limit the possible movement of the distal tip of the device. In contrast, when passing through a fusiform aneurysm, the distal tip of the device must navigate through the open three-dimensional space between the proximal and distal openings of the aneurysm. Because of the relatively less confined space within the aneurysm, it can be extremely difficult to properly align the distal tip to the distal opening.

Typically, the operator can push/pull the intravascular device to move the distal tip forward or backward, and can apply torque to rotate the distal tip. However, if no combination of these maneuvers can properly align the distal tip to the targeted anatomy, such as the distal opening of an aneurysm, the procedure may be seriously delayed or rendered impossible. Accordingly, there is a long felt and ongoing need for intravascular devices providing enhanced navigation capabilities.

BRIEF SUMMARY

An intravascular device, such as a guidewire device, includes a hollow proximal section and a hollow distal section joined to the proximal section and extending distally from the proximal section to form a continuous lumen extending from a proximal end of the device to a distal end of the device. An inner member extends from the proximal end to the distal end and is joined to the distal end. The inner member is translatable within the lumen in response to applied tension. At least the distal section includes a microfabricated cutting pattern that enables deflection of the distal end in response to the application of tension to the inner member.

In preferred embodiments, the cutting pattern of the distal section includes a one-beam or two-beam configuration, though other embodiments may include a three-beam configuration or a configuration of more than three beams. In one embodiment, the distal section includes a one-beam section having a plurality of beams substantially aligned on a single side to form a preferred bending direction. For example, the substantially aligned beams may be disposed at the most distal section of the device adjacent the distal end. This arrangement can beneficially provide reliable and predictable deflection of the distal end of the device when tension is applied to the inner member.

The intravascular device may be constructed of any suitable medical grade materials. Some embodiments include at least one of a proximal section formed as a stainless steel tube, a distal section formed of a nickel-titanium alloy, and an inner member formed of stainless steel. The inner member may be a ground stainless steel core that has a wider cross-sectional diameter at a more proximal section and a narrower cross-sectional diameter at a more distal section.

The intravascular devices described herein may be utilized in any medical procedure requiring passage into the vasculature. Certain embodiments are particularly beneficial in procedures with difficult navigation challenges, such as those requiring passage deep into the neurovasculature and/or when trying to navigate through a fusiform aneurysm. For example, when attempting to navigate through a fusiform aneurysm from the proximal opening to the distal opening, it can be difficult to maneuver through the open three-dimensional space of the aneurysm to reach the distal side. Having additional control over navigation of the device can enable the operator to get past the aneurysm and continue navigating the vasculature. The additional movement, particularly when combined with predictable response as a result of defined distal section cutting patterns, can be the difference between a successful and unsuccessful procedure.

Using a conventional guidewire device, an operator is typically limited to pushing/pulling the device and rotating the device to navigate the patient's vasculature. In some circumstances, such as when passing through an aneurysm, the limited control over navigation can make it extremely difficult to align the distal tip in the desired manner. The additional navigational control offered by the features described herein provides another option for moving the device into proper orientation with respect to patient anatomy. In certain applications where simple push/pull and rotate movements are insufficient to properly guide the device, the additional option of selectively deflecting the tip may be enough to overcome the navigation impediment to allow the device to reach the target.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION

I. Introduction

The present disclosure relates to intravascular devices having features that provide enhanced navigation capabilities. In particular, embodiments are described herein which include a selectively deflectable tip for enabling additional navigation control of the device through vascular anatomy. In the following description, many examples are provided in the context of a guidewire device. It will be understood, however, that the same concepts may be readily applied to a micro catheter application. Accordingly, the concepts and features described herein are not intended to be limited to any particular form of intravascular device.

Further, although many of the following examples are described in the specific context of passing through an aneurysm in a neurovascular procedure, it will be understood that the described embodiments are not limited solely to such applications. The intravascular device embodiments described herein may therefore be utilized in other applications where the enhanced navigation capabilities of the device may be advantageous.

II. Deflectable Tip Components

Figure 1A:
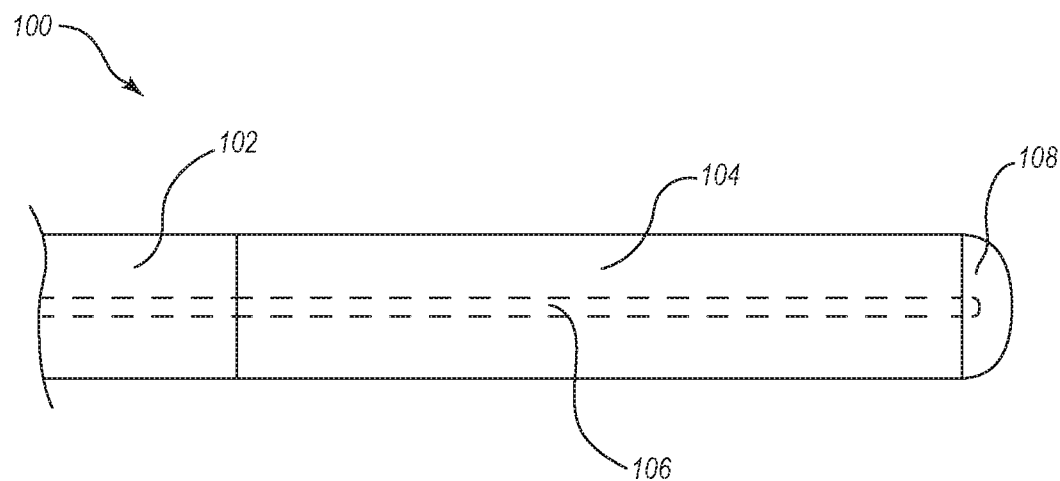
FIGS. 1A and 1B illustrate an exemplary embodiment of a guidewire device having features providing selective deflection.
Figure 1B:
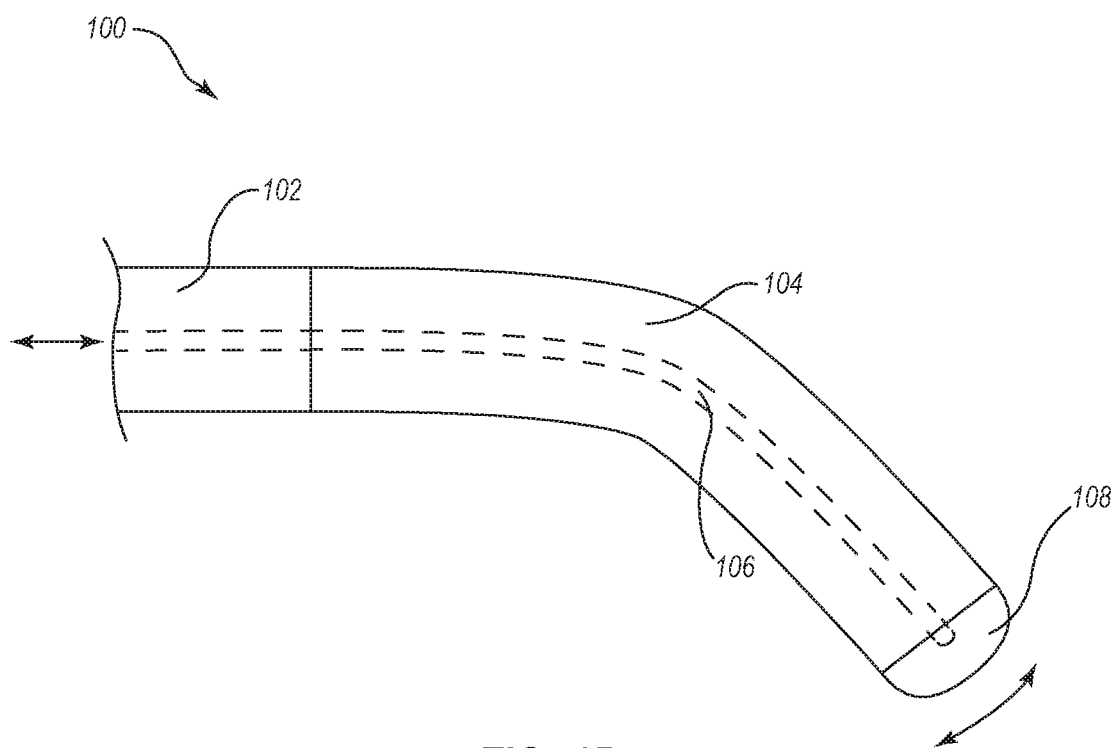

FIGS. 1A and 1B illustrate a distal region of an exemplary guidewire device 100. The device 100 includes a proximal section 102 and a distal section 104 which together form an elongated hollow member. The device 100 also includes an inner member 106 extending from a proximal end (not shown) through the proximal section 102 and through the distal section 104 to attach to a distal tip 108. The distal tip is preferably formed as a polymer adhesive, though other embodiments may additionally or alternatively utilize soldering, welding, fixture hardware, or other suitable attachment means.

As shown in FIG. 1B, the inner member 106 is translatable within the lumen formed by the proximal and distal sections 102, 104, such that the application of tension or compression to the inner member 106 causes the distal section to deflect. Tension or compression may be applied as a result of a user respectively pulling or pushing the inner member 106 at the proximal end of the device and/or operating a control (e.g., dial, button, slider) operatively connected to the inner member 106.

Various materials may be utilized for the construction of the guidewire device. In one preferred embodiment, the proximal section 102 is formed as a stainless steel hypotube, the distal section 104 is formed as a nickel titanium alloy, and the inner member 106 is formed as a stainless steel wire.

In the illustrated embodiment, the inner member 106 is formed as a wire of substantially uniform diameter along its length. In such embodiments, the wire preferably has a diameter that provides sufficient structural integrity and strength but that is small enough to allow sufficient flexibility of the device at the distal end. The wire may have, for example, a diameter of about 0.0002 inches to about 0.005 inches, or about 0.003 inches.

In alternative embodiments, the inner member 106 is formed as a ground core having a diameter that is wider at more proximal sections and that tapers to a narrower diameter at the distal end (e.g., tapers to about 0.002 inches at the distal end). Such embodiments beneficially allow for good flexibility at the distal end of the device while providing more structure for maintaining integrity at more proximal sections of the device. For example, the inner member 106 may have a diameter of about 0.006 to about 0.010 inches for most of its length within the more proximal sections of the device, with a series of one or more tapering sections that reduce the diameter as the inner member 106 gets progressively closer to the distal end.

In contrast to conventional steerable guide sheaths/catheters that include pull wires extending through the circumferential wall of the device, the inner member 106 of the devices described herein extends through the inner lumen of the device. This enables selective deflection/steering of the distal end of much smaller devices, such as those suitable for passage deep into the neurovasculature. At these relatively small diameters, it would be impractical or impossible to provide pull wires within the thickness of the circumferential wall of such a device.

The embodiments shown in FIGS. 1A and 1B beneficially enable the tip of the guidewire device 100 to be selectively deflected to assist in navigating the patient's tortuous vasculature. The distal section 104 may be micro-fabricated to provide for preferential directional bending. In this manner, when translation (tension or compression) is applied to the inner member, there is a consistent, expected resulting deflection that occurs at the distal section 104 of the device.

A variety of different distal section configurations can be utilized to provide a desired response to the adjustment to inner member tension. The cutting patterns described below in relation to FIGS. 4A through 11C may be utilized in any combination to provide the distal section with a bending response that matches particular user preferences and/or application needs. For example, leaving the majority of beams on one side of the distal section following a microfabricated cutting process will provide a preferred bending direction to the distal section. Different arrangements of sections having preferred bending cutting patterns and uniform bending sections can result in the formation of various compound curves, corkscrew shapes, hook-like shapes, and the like. In some embodiments the proximal section may also be micro-fabricated with one or more cut patterns. Typically, the proximal section will be configured to have greater relative rigidity than the distal section.

Figure 2A:
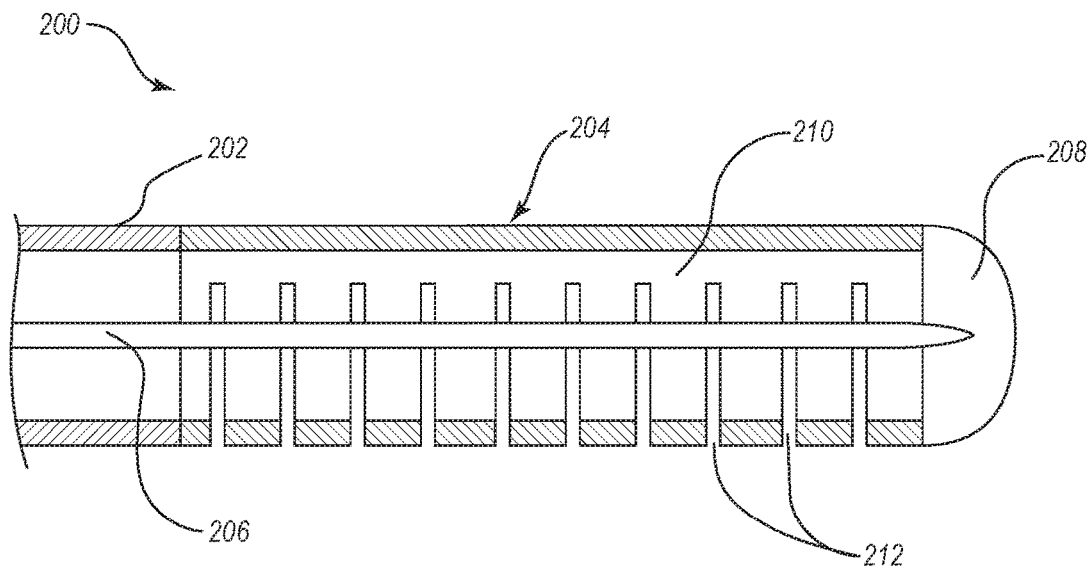
FIGS. 2A and 2B illustrate another embodiment of a guidewire device including a one-beam configuration where beams are substantially aligned on a single side to form a preferred bending direction.
Figure 2B:
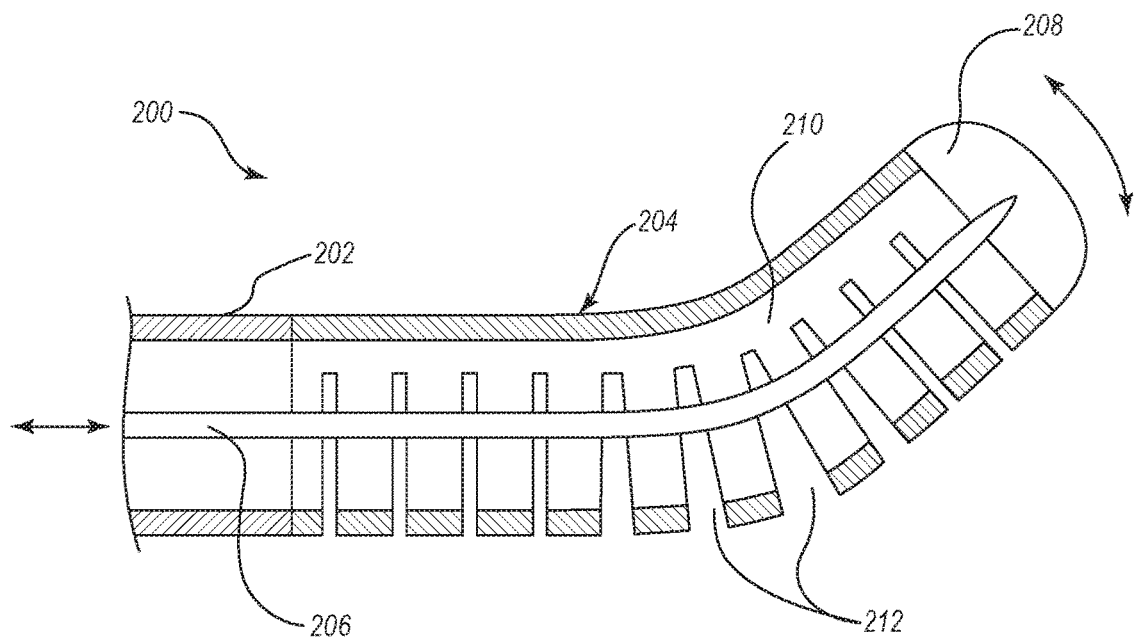

FIGS. 2A and 2B illustrate in cross-section an embodiment of a guidewire device 200 with a distal section 204 having a one-beam configuration with the beams 210 arranged on a single side to form a "spine" of the distal section 204. This arrangement leaves the open fenestrations 212 on the opposite side of the beams 210. As shown, the guidewire device 200 is constructed in a similar fashion to the embodiment of FIGS. 1A and 1B, and includes a proximal section 202, an inner member 206, and a distal end 208.

As shown in FIG. 2B, when tension is applied to the inner member 206, the distal section 204 will deflect away from the side where the open fenestrations 212 are aligned and toward the spine formed by the aligned beams 210. The space and increased flexibility provided by the fenestrations 212 allows the distal section 204 to preferentially bend in the illustrated direction. These features beneficially enable reliable deflection of the distal tip when the inner member 206 is actuated. In contrast, a device not having aligned fenestrations may deflect less predictably and/or be too rigid to easily and selectively deflect.

Although the embodiment shown in FIGS. 2A and 2B represents one presently preferred embodiment, other embodiments may include variably spaced (non-aligned) beam arrangements. For example, some cut patterns may result in beam arrangements that are sufficiently flexible to provide effective deflection of the distal section 204 even though the beams are not substantially aligned.

An alternative embodiment includes pre-shaping the distal tip of the guidewire device such that the application of tension to the inner member leads to a straightening and/or stiffening effect, rather than causing the distal tip to bend. For example, a guidewire device may be formed to be biased toward a pre-curved shape such as in FIG. 2B. The inner member 206 can then be manipulated to move the distal section 204 toward a relatively straighter position such as in FIG. 2A.

Figure 3:
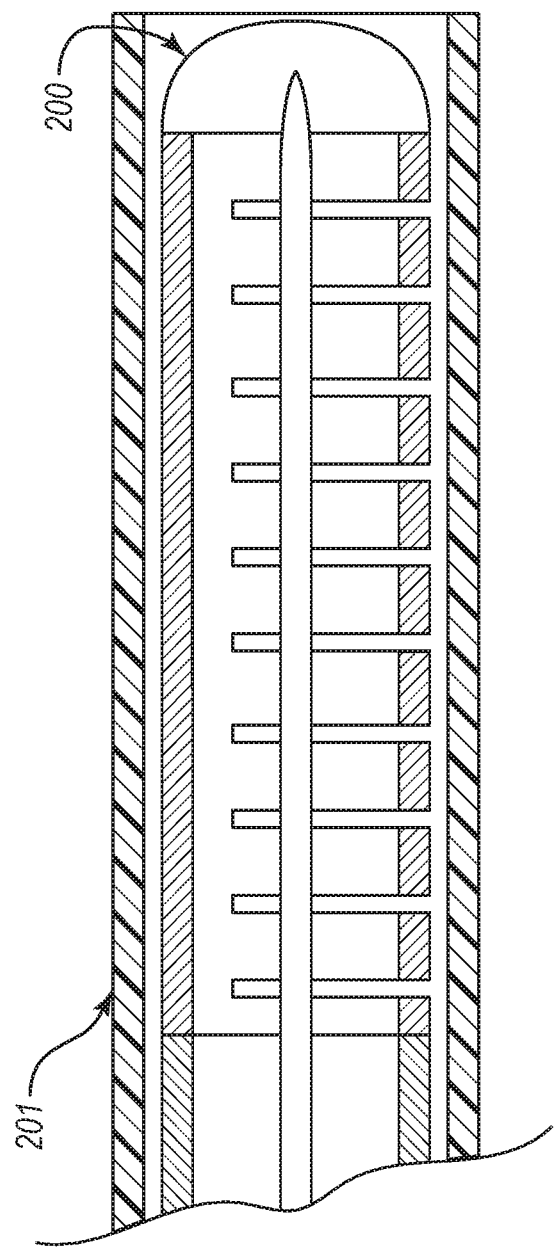
FIG. 3 illustrates the device of FIGS. 2A and 2B nested within a micro catheter.

FIG. 3 illustrates an implementation where the guidewire device 200 is utilized in conjunction with a micro catheter 201. As shown, the guidewire device 200 is positioned within the micro catheter 201. By translating the selectively deflectable portion of the guidewire device 200 so that it coincides with a portion of the micro catheter 201 that is desired to be bent, and by manipulating the inner member of the guidewire device 200, the resulting deflection of the distal section of the guidewire device 200 can be translated to the micro catheter 201.

This type of maneuver can beneficially provide an operator with additional navigation options and abilities. For example, when trying to navigate through an aneurysm from the proximal opening to the distal opening, it can be difficult to maneuver through the open three-dimensional space of the aneurysm to reach the distal side. Having additional control over navigation of the device can enable the operator to get past the aneurysm and continue navigating the vasculature. The additional movement, particularly when combined with predictable response as a result of defined distal section cutting patterns, can be the difference between a successful and unsuccessful procedure.

Using a conventional guidewire device, an operator is typically limited to pushing/pulling the device and rotating the device to navigate the patient's vasculature. In some circumstances, such as when passing through an aneurysm, the limited control over navigation can make it extremely difficult to align the distal tip in the desired manner. The additional navigational control offered by the features described herein provides another option for moving the device into proper orientation with respect to patient anatomy. In certain applications where simple push/pull and rotate movements are insufficient to properly guide the device, the additional option of selectively deflecting the tip may be enough to overcome the navigation impediment to allow the device to reach the target.

The intravascular devices described herein may be any length necessary for navigating a patient's anatomy to reach a targeted anatomical area. An intravascular device typically has a length ranging from about 150 to 350 cm, but the principles described herein can readily be applied to devices having shorter or longer lengths as well.

III. Exemplary Cut Patterns

A. Beam Configurations

Embodiments described herein may include cut patterns which form fenestrations arranged to increase flexibility of the device while maintaining good torquability. Cut patterns described herein may have different configurations defined by the number of resulting longitudinal beams resulting from each set of cuts at a given longitudinal position along the device. For example, in a "two-beam" configuration, each cut location along the length of the device includes a pair of opposed cuts resulting in a pair of opposed, axially extending beams. Typically, the two beams within the resulting beam pair are symmetrically spaced about the circumference of the catheter (i.e., spaced about 180 degrees apart), though in other embodiments they may be differentially circumferentially spaced. Likewise, the triad of beams in a three-beam configuration are typically symmetrically spaced about the circumference by about 120 degrees, the set of beams in a four-beam configuration are typically spaced about the circumference by about 90 degrees, etcetera, though other embodiments may include differential circumferential spacing.

All other manufacturing parameters being equal (e.g., similar materials, cut depth, cut spacing, etc.), a configuration having a greater number of beams will be less flexible but have greater capacity for transmitting torque. Embodiments may include multiple sections each having a different beam configuration to provide different respective flexibility characteristics and a desired flexibility gradient across the length of the device. At the same time, a particular section having a particular beam configuration can include cuts arranged to provide a flexibility gradient within the particular section itself. For example, longitudinal spacing between cuts may be progressively less at areas closer to the distal end of the device. In this manner, a device may be configured to provide a desired flexibility profile across the length of the device by including both inter- and intra-sectional flexibility gradients.

Figure 4A:
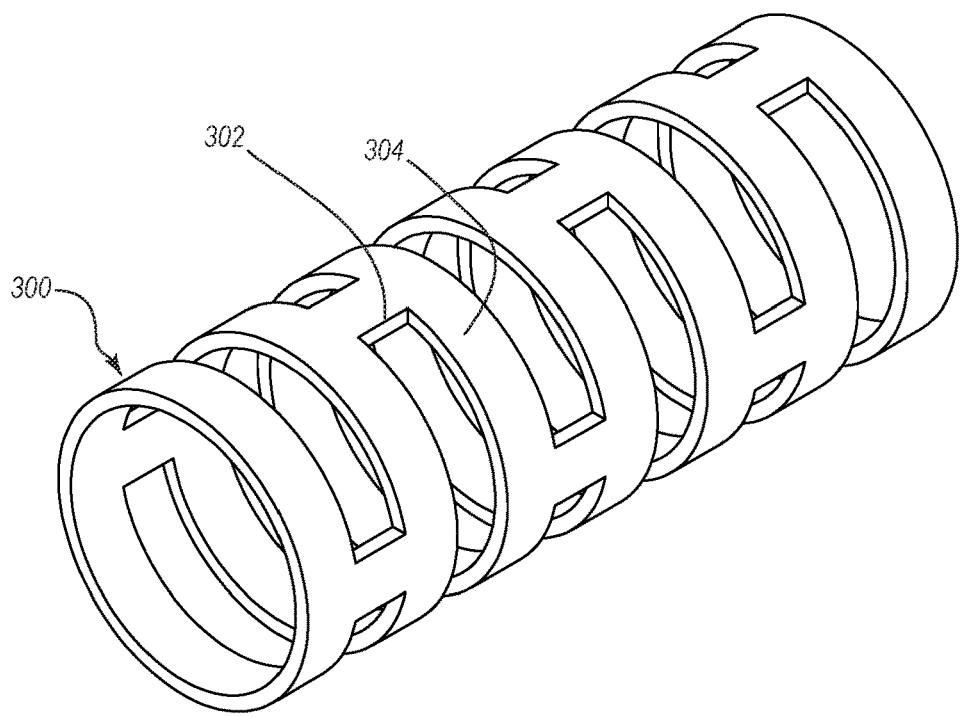
FIGS. 4A through 4D illustrate various beam configurations that may be utilized in various combinations to provide desired bending characteristics in the intravascular device.
Figure 4B:
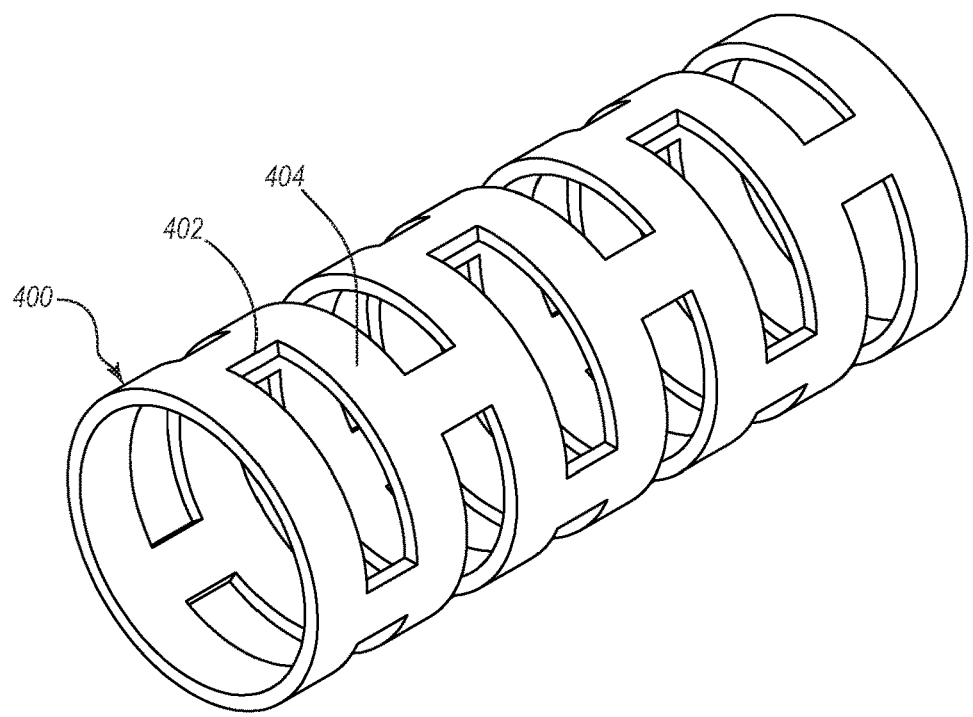
Figure 4C:
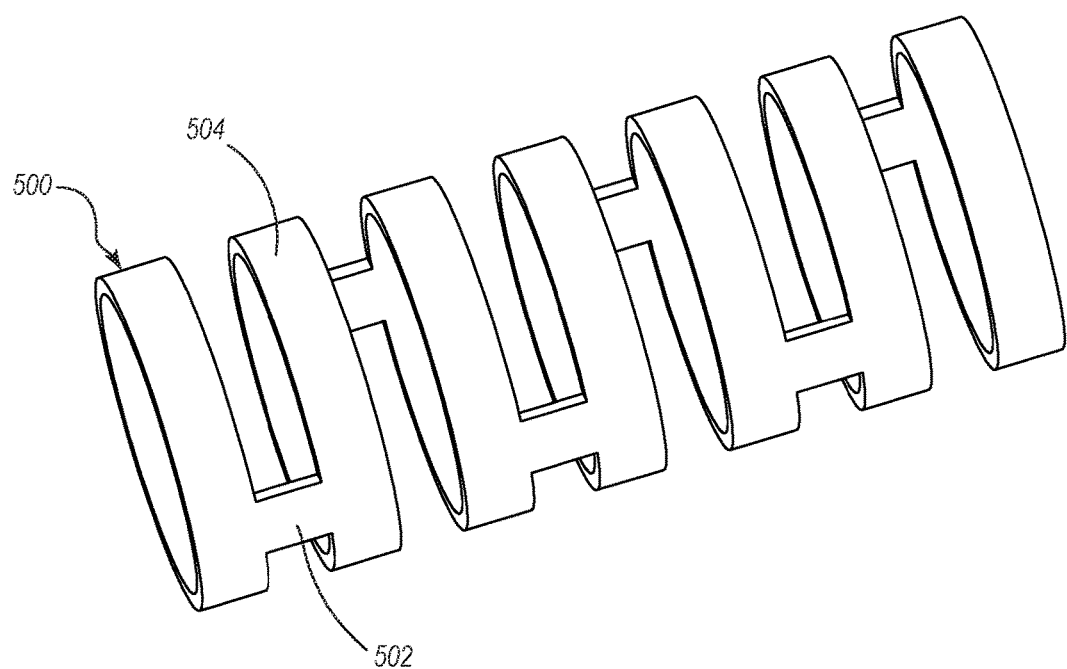
Figure 4D:
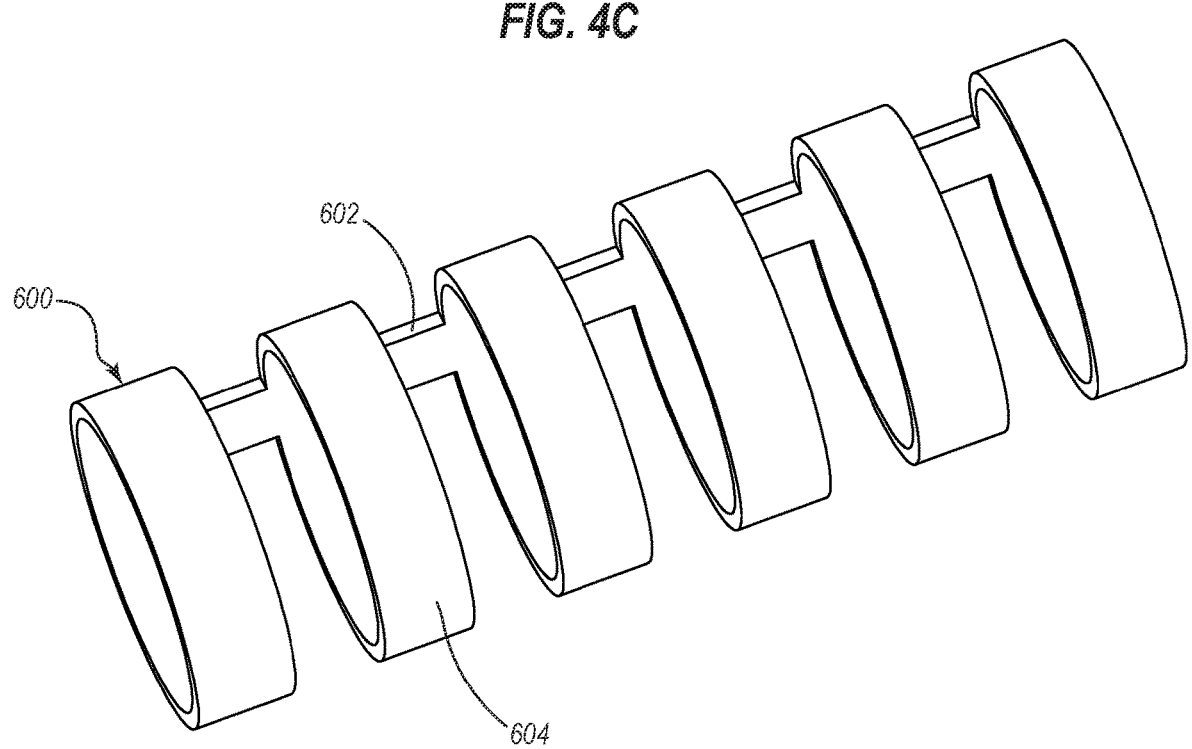

FIGS. 4A through 4D illustrate various embodiments of cut patterns which may be utilized in the devices described herein. FIG. 4A shows a "two-beam" configuration, FIG. 4B shows a "three-beam" configuration, and FIGS. 4C and 4D show different versions of a "one-beam" configuration. Other embodiments may include configurations of more than three resulting beams per cut location (e.g., a "four-beam" cut pattern, "five-beam" cut pattern, etc.). All other manufacturing parameters being equal, the higher the number of resulting beams at each cut position, the lower the flexibility and the higher the torquability of the section.

As shown in FIG. 4A, an elongated section 300 includes a plurality of axially extending beams 302 and circumferentially extending rings 304. The elongated section 300 has a two-beam cut pattern because two circumferentially opposing beams 302 are disposed between each pair of adjacent rings 304. The opposing cuts in each cut pair will typically have equal depth, leaving each beam of the resulting beam pair symmetrically circumferentially spaced. Other embodiments may include cut pairs with opposing cuts of differential depth. The greater the difference between the depths of opposing cuts in each cut pair, the closer together circumferentially the beams of the resulting beam pair will be, and therefore the more similar functionally the two-beam cut will be to a one-beam cut.

The illustrated embodiment shows a distribution of beam pairs angularly offset by 90 degrees from one pair to the next along the axis of the member. In alternative embodiments, the angular offset may be more or less than 90 degrees. For example, the angular offset may be about 5, 15, 30, 45, 60, 75, 80, or 85 degrees (in either direction), or may include a plurality of different offset values.

In some embodiments, an angular offset is applied at each successive beam pair. In other embodiments, an angular offset is applied at each successive "segment," with each segment including more than one beam pair. As used herein, a "segment" is a repeating structural unit of the catheter section. In some embodiments, a single segment can be defined as a first pair of opposing beams 302 disposed between two adjacent rings 304 (one proximal ring and one distal ring) and a second pair of opposing beams extending from the distal ring and being rotationally offset by about 90 degrees from the first pair of opposing beams 302. Thus, an embodiment having such segments and having a rotational offset of 5 degrees from segment to segment would have a first beam pair at a 0 degree position, a second at 90 degrees, a third at 5 degrees, a fourth at 95 degrees, etcetera.

FIG. 4B illustrates an elongated section 400 having a plurality of beams 402 and rings 404 arranged in a three-beam configuration. In this embodiment, each triad of beams at each cut location is symmetrically circumferentially spaced by 120 degrees. An angular offset of 60 degrees is applied at each successive cut location. As with the two-beam configuration described above, the beams of a triad need not be symmetrically spaced. Likewise, an angular offset of more or less than 60 degrees may be used, and it may be applied at each successive cut location or at each successive segment. In a three-beam configuration, for example, a segment may be defined as a first triad of beams 402 disposed between two adjacent rings 404 (one proximal ring and one distal ring) and a second triad of beams extending from the distal ring and being rotationally offset by about 60 degrees from the first triad 402.

FIG. 4C illustrates an elongated section 500 having a series of beams 502 and rings 504 arranged in a one-beam configuration. An angular offset of 180 degrees is applied at each successive cut location. As with the other configurations described above, an angular offset of more or less than 180 degrees may be used, and it may be applied at each successive cut location or at each successive segment. In a one-beam configuration, for example, a segment may be defined as a first beam 502 disposed between two adjacent rings 504 (one proximal ring and one distal ring) and a second beam extending from the distal ring and being rotationally offset by about 180 degrees from the first beam 502.

FIG. 4D illustrates another embodiment of an elongated section 600 having a series of beams 602 and rings 604 arranged in a one-beam configuration. In this embodiment, the cuts are provided so that the beams 602 are aligned along one side of the section length, rather than having an angular offset. Such an embodiment can beneficially provide preferential bending in one direction (i.e., toward the aligned beams 602).

Figure 5:
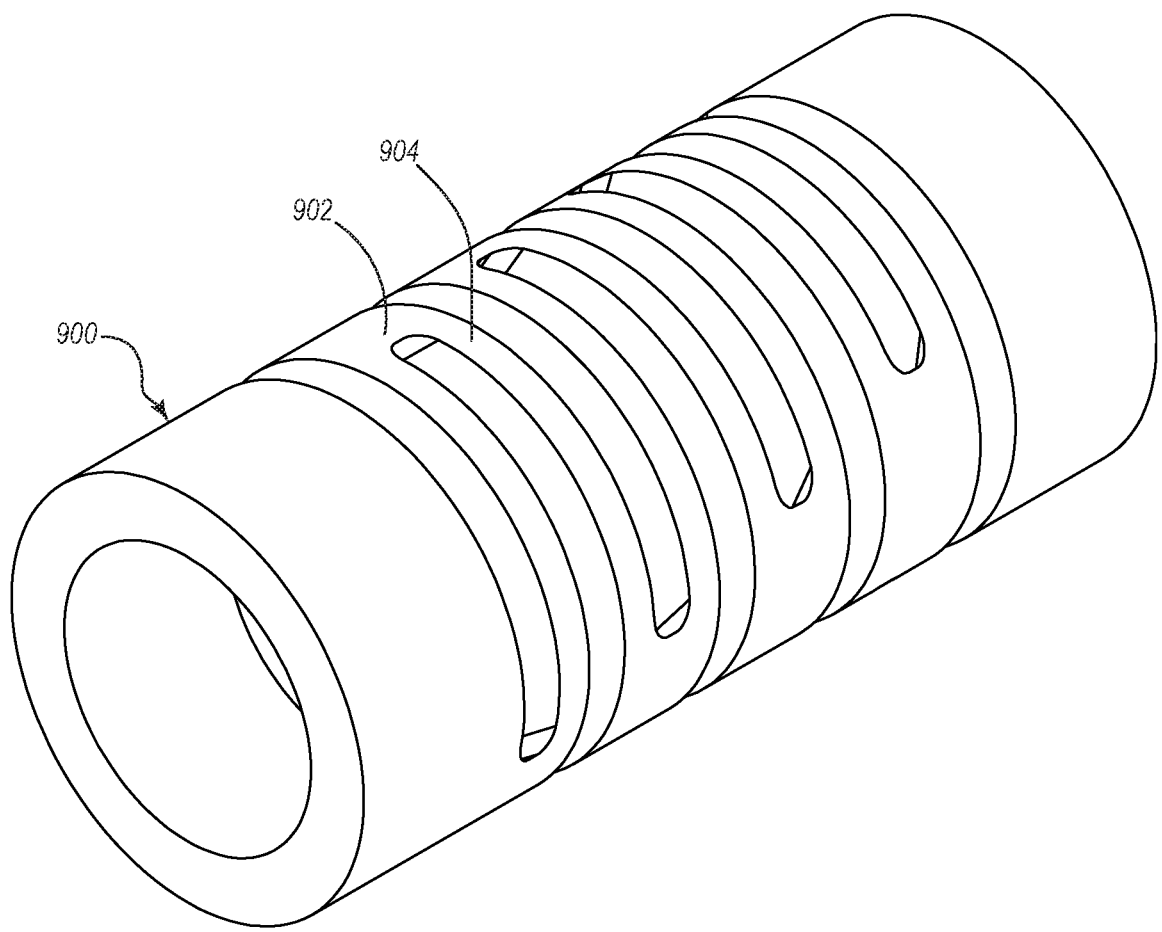
FIG. 5 illustrates a cutting pattern with a helical arrangements of beams.

FIG. 5 illustrates an embodiment of a typical helical cut pattern intended to minimize preferred bending directions. As shown, a rotational offset is applied at each successive segment of the elongate member 900 to form the helical pattern. FIG. 5 illustrates a helical one-beam cut pattern where each cut leaves a single beam 902 between each set of adjacent rings 904. Although successive beams are shown as being offset by about 180 degrees, each successive pair is part of a "segment," and each successive segment is shown as having a rotational offset of about 5 degrees The rotational offset may be applied from segment to segment, as shown in FIG. 5, or may alternatively be applied at each successive cut. This type of helical arrangement may also be used in embodiments having different cut configurations. For example, a two-beam configuration may have a helical arrangement with rotational offset applied at each successive segment or at each successive cut pair.

B. Distributed Patterns

Figure 6:
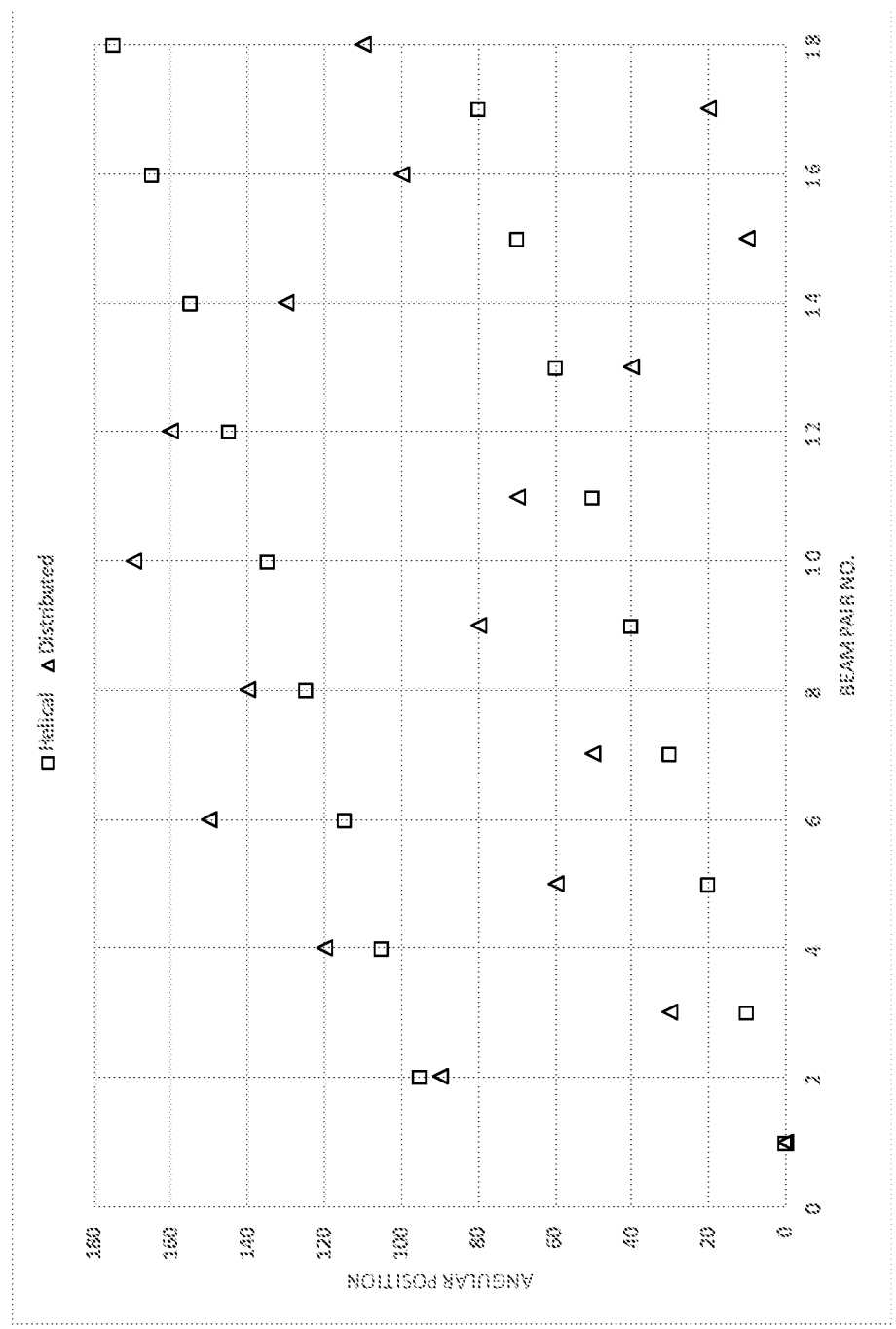
FIG. 6 graphically illustrates a distributed cut pattern and shows a typical helical pattern for comparison.

Some embodiments may include a section having a distributed beam arrangement resulting from a non-helical and non-linear cut pattern. This type of pattern effectively eliminates or minimizes preferred bending directions. FIG. 6 graphically compares one example of a distributed pattern with a conventional helical pattern. As shown, the helical cut pattern applies a constant rotational offset from segment to segment along the length of the elongated member. The distributed cut pattern applies a rotational offset that effectively distributes bending axes without relying on a helical pattern.

The helical and distributed patterns graphically shown in FIG. 6 are for devices having a two-beam configuration. Since a typical two-beam configuration will space each beam pair apart by about 180 degrees, a beam pair at a given position will be indistinguishable from a beam pair rotationally offset by 180 degrees. Accordingly, the possible rotational positions for beam pairs are shown as ranging from 0 to 180 degrees, with the zero and 180 degree positions being equal to one another. Other distributed pattern embodiments may exhibit different rotational spacing. For example, a one-beam configuration will typically be distributed across the full available 360 degree rotational space, and a three-beam pattern will typically exhibit 120 degree symmetry, and therefore be distributed across a 120 degree rotational space.

The distributed pattern shown in FIG. 6 is "non-helical." A helix is commonly defined as following a curve on a conical or cylindrical surface that would become a straight line if the surface were unrolled into a plane. Using the helical cut pattern shown in FIG. 5 as an example, any curved lines tracing the arrangement of the segments along the length of the elongated member 900 would form straight lines if the elongated member 900 were cut open and "unrolled" into a plane. In contrast, in the distributed pattern shown in FIG. 6, there are no lines tracing the arrangement of the beams/segments that form straight lines.

Given a starting beam pair arbitrarily assigned to a zero degree position, successive beam pairs are rotationally offset to maximize the radial distribution of beam positions across the available 180 degree rotational space as quickly as possible (i.e., in as few cuts as possible). However, in the illustrated embodiment, a rotational offset limit is also applied to prevent the formation of rigid spacing artifacts (discussed further below with respect to FIGS. 9 and 10).

The rotational offset limit defines a limit on the acceptable rotational "jump" from one beam pair to the next or from one segment to the next. A rotational offset limit with a value of about 10 to 30 degrees from one segment to the next, or a rotational offset limit that rotates successive beam pairs by 90 degrees±that value, has been shown to provide effective distribution of bending axes without causing overly rigid spacing artifacts. For example, the rotational offset limit may restrict rotation from one beam pair to the next to a value within a range of about 60 to 120 degrees, or about 70 to 110 degrees, or about 80 to 100 degrees. Other embodiments may utilize other rotational offset limits, or may even omit the rotational offset limit, depending on particular product and/or application needs. For example, the rotational offset limit may be raised to a value higher than 30 degrees if the resulting spacing artifacts are acceptable for a particular application.

The exemplary distributed cut pattern illustrated in FIG. 6 utilizes a rotational offset limit of 30 degrees. As shown, a first beam pair is positioned at an arbitrary 0 degree position, and the second beam pair is positioned at 90 degrees. The greatest remaining gaps in the available 180 degree space are between 0 and 90 degrees and between 90 and 180 degrees (where 0 and 180 degrees represent the same position). Placing the next beam pair near a midpoint of one of these gaps, such as at 45 degrees, would best distribute the bending axes of the device. However, placing the next beam pair at 45 degrees would violate the rotational offset limit of 30 degrees. The next beam pair is therefore placed to be close to the midpoint of a remaining gap without violating the rotational offset limit. In this example, the third beam pair is placed at 30 degrees. The fourth beam pair is placed at 120 degrees, which is 90 degrees from the third beam pair.

In this particular example, every other beam pair is offset 90 degrees from the previous beam pair. Alternative embodiments need not necessarily follow this particular pattern. For example, where the illustrated embodiment is an example of varying the applied offset from segment to segment, other embodiments may apply the variable offset from beam pair to beam pair.

Continuing with the example distribution of FIG. 6, the largest remaining positional gaps are now between 30 and 90 degrees and between 120 and 180 degrees. The fifth and sixth beam pairs are placed at 60 and 120 degrees, respectively. The remaining positional gaps are now located every 30 degrees (i.e., between 0 and 30 degrees, between 30 and 60 degrees, between 60 and 90 degrees, etc.). As the pattern continues, remaining angular positions are filled in a manner that radially spaces beam pairs as fast as possible without violating the rotational offset limit.

In the illustrated example, the available angular positions are provided at a granularity of 10 degrees. In other words, all angular positions may be considered as filled when each 10 degree increment has been filled. The illustrated pattern may therefore includes beam pairs positioned at approximately every 10 degree position before resetting. Such an arrangement is referred to herein as having a "positional granularity" of 10 degrees. Alternative embodiments may utilize a different positional granularity, such as a granularity of 0.1, 0.5, 1, 3, 5, 10, 15, 18, 20, 25, or 30 degrees, for example.

The exact positioning illustrated may be adjusted, and it will be understood that the pattern shown in FIG. 6 is illustrative only. For example, the positional gaps may be filled using a different particular sequence as long as rotational jumps are within the predetermined rotational offset limit. Preferably, when filling in gaps between rotational positions, the next beam pair is positioned to be close to the approximate center of the largest remaining positional gap without violating the rotational offset limit. For example, where a gap exists between the 0 degree position and the 30 degree position, the segment may be positioned at the 10 to 20 degree position.

Further, alternative embodiments may utilize a positional granularity that fills in positions of more or less than 10 degrees. Where fewer segments are used before resetting the pattern, the size range of each suitable position will be larger, and where more segments are used before resetting the pattern, the size ranges will become smaller. Some embodiments may include about 6 to 36 beam pairs, or about 10 to 18 beam pairs, before the availability of filled angular positions within the 180 degree radial space is reset. Other embodiments may include many more beam pairs before available positions are reset. As the predetermined positional granularity is lowered, the number of beam pairs needed to fill all available angular positions will rise. Thus, a device having a positional granularity of 1 degree will use 180 beam pairs to fill 180 available angular positions.

Moreover, because there are multiple ways of filling available angular positions according to the predetermined parameters (e.g., positional granularity and rotational offset limit) of the selected distributed pattern, the distributed cut pattern need not identically repeat itself after resetting. Therefore, as used herein, the terms "reset," "resetting," and the like refer to resetting the availability of angular positions within the 180 degree radial space after it has been filled by beam pairs, and the terms do not necessarily imply that the subsequent refilling of angular positions along the next section of the elongated member will exactly repeat the previous pattern. Indeed, in at least some embodiments, the entire length of the distributed pattern may be non-repeating.

It will be understood that the foregoing principles may also be applied to an embodiment having a one-beam arrangement, an embodiment having a three-beam arrangement, or an embodiment having more than a three-beam arrangement. The same principles described above may be applied to a one-beam embodiment, except that the range of angular positions to fill will extend to 360 degrees. Likewise, the same principles may be generally applied to a three-beam embodiment, except that the range of angular positions to fill will typically extend to 120 degrees.

C. Imperfect Ramp Patterns

Figure 7:
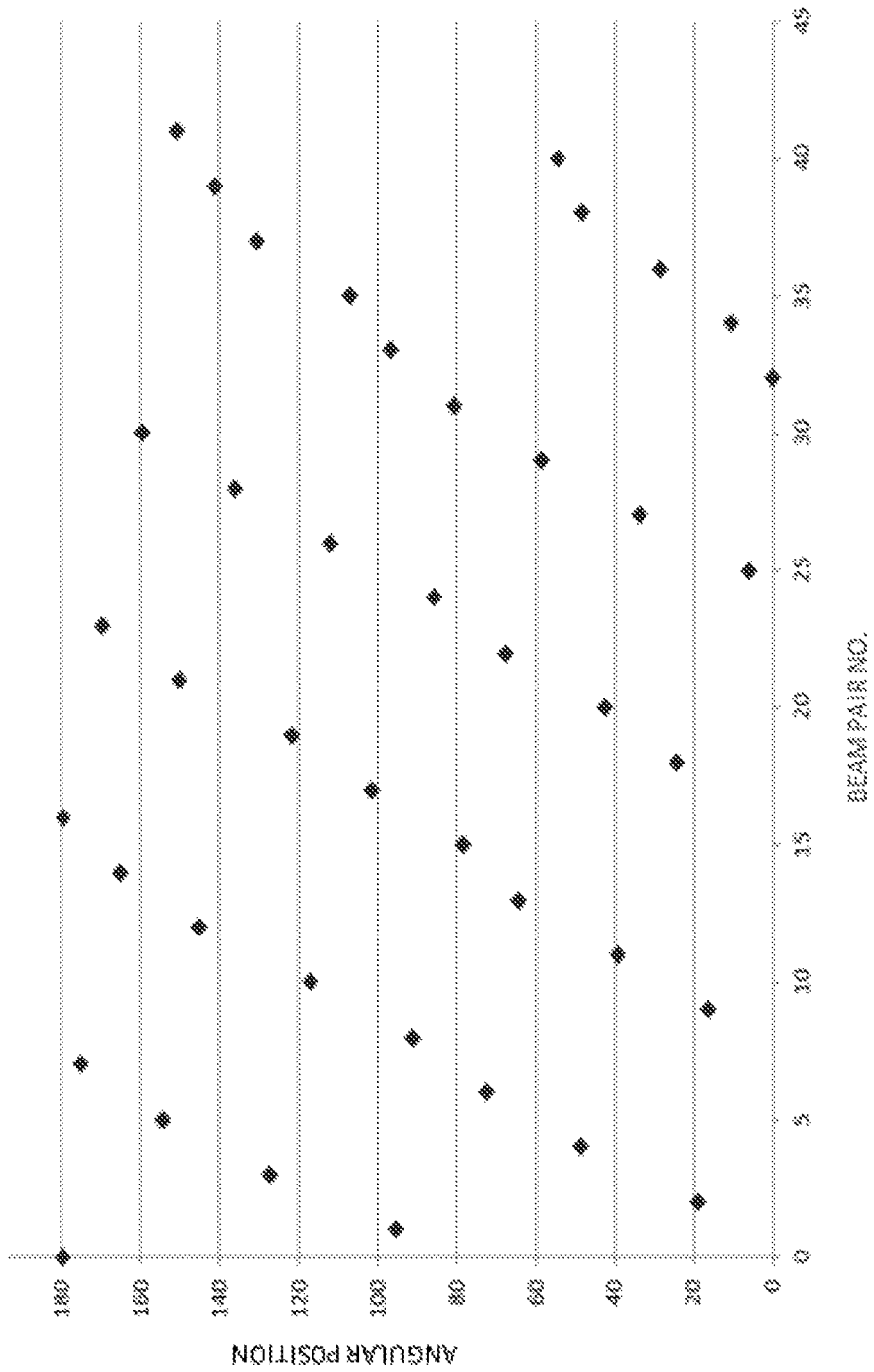
FIG. 7 graphically illustrates an imperfect ramp cut pattern.

FIG. 7 graphically illustrates another embodiment of a non-helical cut pattern formed by intentionally disrupting an otherwise helical pattern with a series of purposefully designed imperfections. This type of cut pattern is referred to herein as an "imperfect ramp" pattern. The intentional divergences of an imperfect ramp pattern beneficially function to reduce or prevent preferred torsional and curvature relics inherent in a true helical arrangement. As shown, segments are arranged such that no three successive beam pairs or segments are spaced according to the same rotational offset. In other words, no three beam pairs or segments are arranged so as to form a straight line if the cylindrical elongated member were unrolled into a plane.

In contrast to the imperfect ramp patterns of FIG. 7, a true helical pattern is typically formed by rotationally offsetting each successive segment or each successive beam pair by a constant value. For example, a true helical pattern in a two-beam structure may be formed by rotationally offsetting each successive cut pair by a constant value of 5 degrees, 85 degrees, 95 degrees, or some other constant value that is not a multiple of 90 degrees.

In an imperfect ramp cut pattern, the modifying value is intentionally made variable rather than constant. For example, as in FIG. 7, an imperfect ramp pattern may be formed by rotationally offsetting each successive beam pair by a constant value±a variable modifying value. A rotational offset that includes a constant value±a variable modifying value is referred to herein as an "imperfect rotational offset."

The variable modifying value may range from 5 to 15 degrees. In other embodiments, the variable modifying value may range from 2.5 to 30 degrees, or some other range suitable for the intended purpose of the resulting device. The variable modifying value is preferably randomly selected at each segment or beam pair to which it is applied, with upper and lower bounds of the random selection being defined by the modifying value range (e.g., 5 to 15 degrees). The constant value portion of the offset is typically 180 degrees in a one beam pattern, 90 degrees in a two-beam pattern, 60 degrees in a three-beam pattern, etcetera.

Alternative embodiments may apply the imperfect ramp pattern between segments of different sizes and/or between segments with different internal offsets. For example, some embodiments may include segments having more than two pairs of beams (and more than two corresponding rings) and/or with internal offsets different than 90 degrees. Further, even though the illustrated example shows a two-beam cut pattern where each pair of the opposing cuts results in two circumferentially opposing beams, it will be understood that the distributed offset patterns may also be applied to one-beam cut patterns, three-beam cut patterns, and patterns having more than three beams between adjacent rings.

D. Sawtooth Patterns

Figure 8:
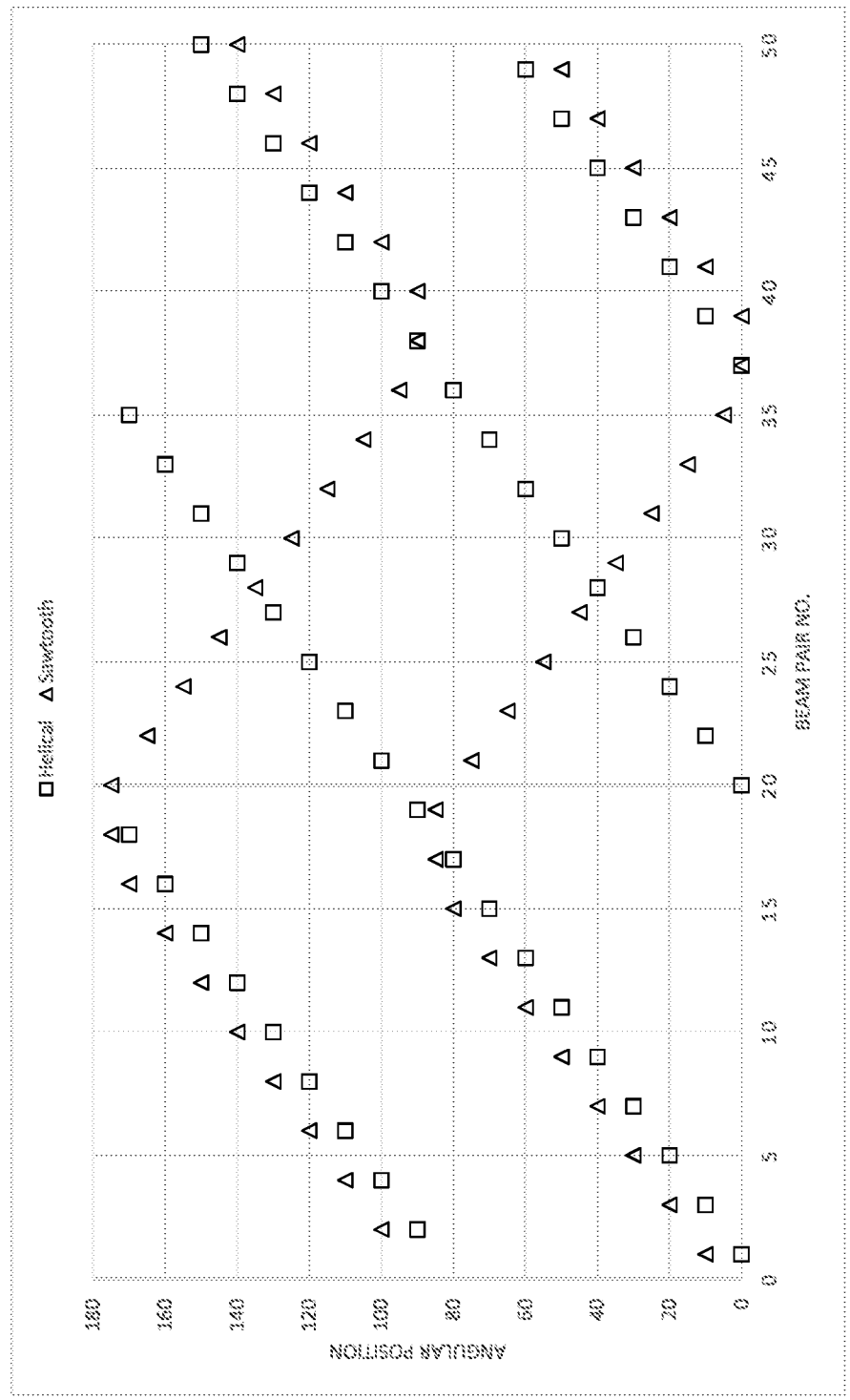
FIG. 8 graphically illustrates a sawtooth cut pattern and shows a typical helical pattern for comparison.

FIG. 8 illustrates another embodiment of a non-helical cut pattern referred to herein as a "sawtooth" pattern. As with other non-helical cut patterns described herein, the sawtooth cut pattern can beneficially avoid preferred bending axes while also limiting preferred curvature directions inherent in helical patterns. In contrast to a helical pattern, a sawtooth cut pattern periodically reverses the direction of the rotational offset.

Both the sawtooth pattern and the helical pattern of FIG. 8 have an angular offset of about 10 degrees between adjacent segments, with each cut pair within each segment offset by 90 degrees. Whereas the helical pattern simply continues with these offset values in the same direction through multiple rotations around the circumference of the elongated member, the sawtooth pattern reaches a first apex position before reversing direction and continuing toward a second apex position. Upon reaching the second apex position, the sawtooth pattern then reverses again and continues back toward the first apex. The pattern then repeats along the desired length of the elongated member.

For example, the first apex position is set at about 90 degrees (i.e., 90 degrees for the first cut pair of the segment and 180 degrees for the second cut pair of the segment). Upon reaching the first apex position, the pattern reverses toward the second apex position. In this embodiment, the second apex position is set at about 0 degrees (i.e., 0 degrees for the first cut pair of the segment and 90 degrees for the second cut pair of the segment). Alternative embodiments may include other apex positions. Given an arbitrary zero degree starting position, the first apex position is less than 360 degrees in a one-beam configuration, less than 180 degrees in a two-beam configuration, less than 120 degrees in a three-beam configuration, and so on. Preferably, the first apex position is about 180 degrees for a one-beam configuration, 90 degrees for a two-beam configuration, 60 degrees for a three-beam configuration, and so on.

As described above, the angular offset from segment to segment in the sawtooth pattern of FIG. 8 is about 10 degrees. In other embodiments of sawtooth cut patterns, the angular offset may be more or less than 10 degrees, such as from about 5 degrees to about 30 degrees. Additionally, or alternatively, portions of the cut pattern between the apexes may include a variable offset. For example, one or more portions between the apexes may include an imperfect rotational offset such as described above in relation to FIG. 7.

Alternative embodiments may apply the sawtooth pattern between segments of different sizes and/or between segments with different internal offsets. For example, some embodiments may include segments having more than two pairs of beams (and more than two corresponding rings) and/or with internal offsets different than 90 degrees. Further, even though the illustrated example shows a two-beam cut pattern where each pair of the opposing cuts results in two circumferentially opposing beams, it will be understood that the distributed offset patterns may also be applied to one-beam cut patterns, three-beam cut patterns, and patterns having more than three beams between adjacent rings.

E. Spacing Artifacts

Figure 9:
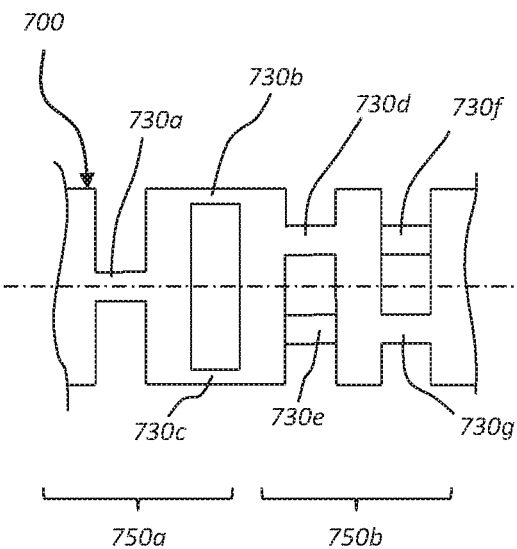
FIGS. 9 and 10 illustrate differences in rotational offsets, showing differences in spacing artifacts resulting from different sizes of rotational offset jumps.

FIG. 9 illustrates an example of an undesirable spacing artifact that may result where a rotational offset limit is not applied. FIG. 9 illustrates a section of an elongated member 700 having a first segment 750a and a second segment 750b. The first segment 750a includes a first pair of beams 730a (only one of which is visible in this view) and second pair of beams 730b and 730c which are offset from the first pair by 90 degrees. The second segment 750b includes a first pair of beams 730d and 730e, and a second pair of beams 730f and 730g which are offset from the first pair by 90 degrees. Each beam within a pair is circumferentially spaced from its corresponding beam by 180 degrees. The second segment 750b is offset from the first segment 750a by 45 degrees, which positions the first pair of beams 730d and 730e off by 45 degrees from the first pair of beams 730a and positions the second pair of beams 730f and 730g off by 45 degrees from the second pair of beams 730b and 730c.

Applying such a 45 degree offset from the first segment 750a to the second segment 750b may at first be considered desirable because it places the bending axes of the second segment 750b in between the bending axes of the first segment 750a. However, the 45 degree jump also results in beam spacing between segments which can leave an overly rigid artifact in a portion of the elongated member 700. In the illustrated member 700, the beam 730d is only spaced from the beam 730b by 45 degrees, whereas the beam 730e is spaced from the beam 730*b* by 135 degrees. Likewise, the beam 730*e* is only spaced from the beam 730*c* by 45 degrees, whereas the beam 730*d* is spaced from the beam 730*c* by 135 degrees. This disproportionate spacing may be undesirable because the region of the elongated member 700 having the smaller spacing may be overly rigid and/or the region having the larger spacing may be overly flexible.

Figure 10:
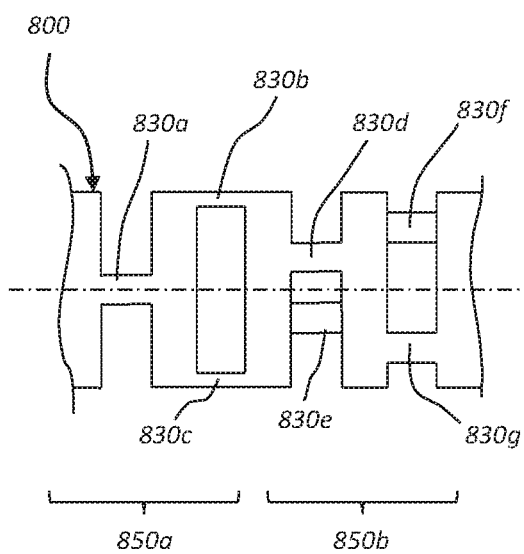

In contrast, a more limited jump in the rotational offset applied from one segment to the next will minimize the discrepancy in beam spacing between segments. For example, FIG. 10 illustrates a section of an elongated member 800 with a more limited rotational offset of about 20 degrees applied between a first segment 850*a* and a second segment 850*b*. As in the elongated member 700 of FIG. 9, the first segment 850*a* includes a first pair of beams 830*a* and a second pair of beams 830*b* and 830*c*, and the second segment 850*b* includes a first pair of beams 830*d* and 830*e* and a second pair of beams 830*f* and 830*g*. However, because the second segment 850*b* is offset from the first segment 850*a* by a more limited 20 degrees, the spacing discrepancy between beams 830*b*, 830*c*, 830*d*, and 830*e* is less pronounced. Beam 830*d* is spaced 70 degrees from beam 830*b*, and beam 830*e* is spaced 110 degrees from beam 830*b*. Likewise, beam 830*e* is spaced 70 degrees from beam 830*c* and beam 830*d* is spaced 110 degrees from beam 830*c*. Thus, although a spacing discrepancy still exists between segments, it may be controlled to a suitable degree by providing an appropriate rotational offset limit.

F. Spiral Patterns

Figure 11A:
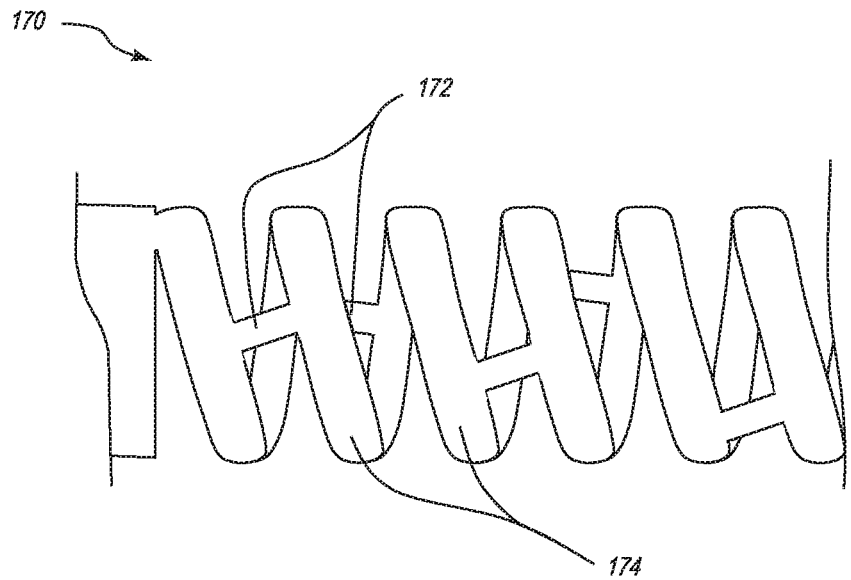
FIGS. 11A through 11C illustrate various spiral cut patterns that may be utilized to provide desired bending characteristics in the distal section of the intravascular device.
Figure 11B:
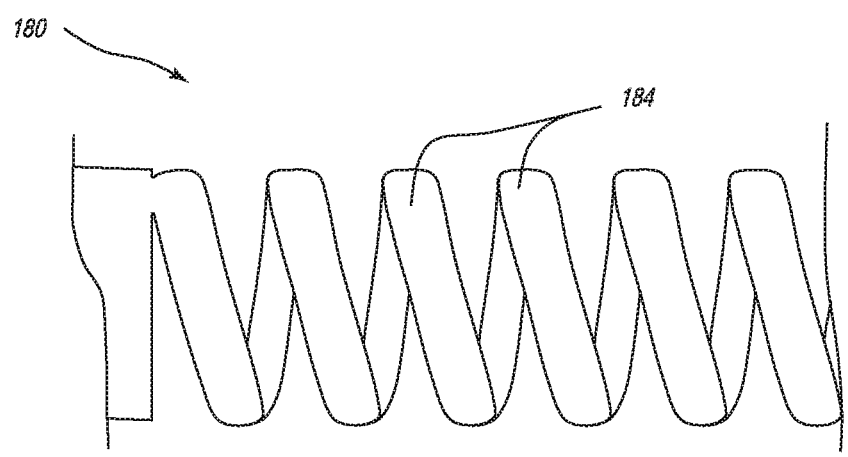
Figure 11C:
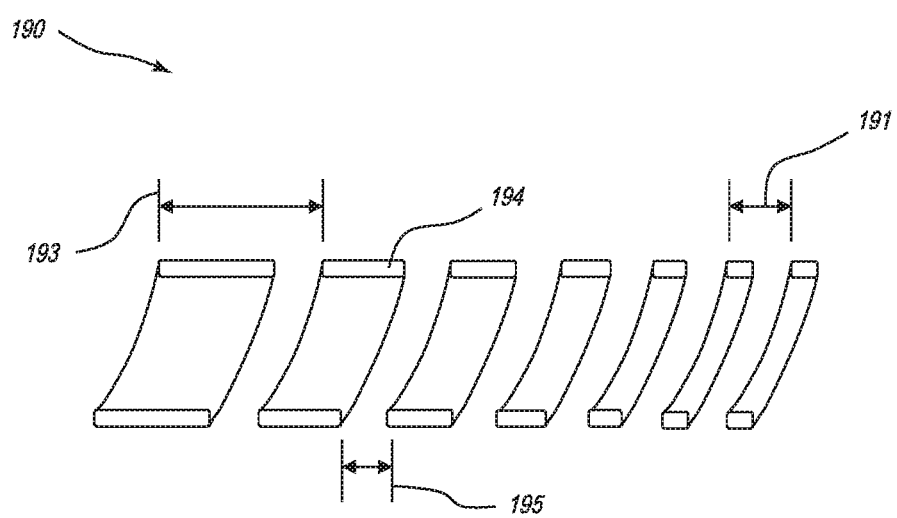

FIGS. 11A through 11C illustrate embodiments of a "spiral" cut pattern that may be included in one or more sections of the device. As shown in FIG. 11A, a section 170 of device is cut to provide an outer body of resulting helically oriented coil members 174, with the pitch of the resulting coil defining the size of the fenestrations. Typically, a spiral cut pattern provides less torquability and more flexibility than a one-beam pattern. As such, in most applications, spiral sections are less beneficial at more proximal sections of the device where torquability concerns are particularly important, but are beneficial at more distal sections, and particularly at or near the distal end of the device, where flexibility concerns become more important.

In preferred embodiments, the spiral cut section 170 forms an integral piece of material with one or more adjacent sections of the elongated device. For example, rather than welding, adhering, or otherwise attaching a separate coil member to another section of the device (which unfavorably introduces potential failure points and increases manufacturing difficulty), the spiral pattern results from a cutting operation performed on the section. In this manner, a single piece of material can be micro-fabricated to include one or more sections of different cut arrangements, in addition to the one or more spiral cut patterns.

The embodiment shown in FIG. 11A also includes a series of bridges 172 that remain between and connect adjacent coil members 174 of the spiral pattern. Such bridges 172 can function to somewhat limit the flexibility of the section 170 relative to a similar spiral pattern omitting such bridges. FIG. 11B, for example, illustrates another spiral cut section 180 that may be included in the hollow elongated member 104. The spiral cut pattern of section 180 omits bridges between coil members 184, and therefore has relatively greater flexibility than the spiral section 170 shown in FIG. 11A (assuming materials, pitch, diameter, wall thickness, and other relevant factors are otherwise substantially equal). Bridges 172 can also be arranged to provide flexibility bias in one or more directions.

In embodiments having bridges 172, such as the embodiment shown in FIG. 11A, the bridges 172 may be spaced about every 45, 60, 75, 90, 105, 120, 135, 150, 165, or 180 degrees around the spiral shape of the device. Greater spacing may also be provided between successive bridges. For example, multiples of 360 degrees may be added to any of the foregoing angle spacing values to provide an even greater spacing arrangement. Less spacing generally limits flexibility to a greater degree, while greater spacing generally provides greater relative flexibility. In some embodiments, spacing of the bridges 172 can vary across the length of the section 170. For example, spacing between the bridges 172 can become progressively greater toward the distal end of the section in order to progressively increase distal flexibility.

Additionally, or alternatively, a spiral cut pattern may be varied along its length to provide desired flexibility characteristics. FIG. 11C illustrates, in cross-sectional view, an embodiment of a section 190 where spacing between spiral cuts is tailored to be progressively narrower as the cuts near the distal end of the section. As shown, the dimension 191 between two of the coil members 194 is smaller at a more distal region than the dimension 193 between more proximally located coil members 192. In the illustrated embodiment, the cut width, indicated by dimension 195, is substantially constant. In alternative embodiments, the cut width 195 may be adjusted as an alternative to or in addition to the progressive changes in coil member size shown by dimensions 191 and 193. Other embodiments may omit progressively changing features, or may include one or more sections including progressively changing features and one or more other sections with substantially constant coil dimensionality.

Typically, assuming that device materials, device size, cut widths (and resulting beam size in the axial direction), cut spacing (and resulting ring size in the axial direction), and cut depth (and resulting beam width in the circumferential direction) are the same, a spiral cut pattern omitting bridges will provide greater flexibility than a spiral cut pattern with bridges, which will provide greater flexibility than a one-beam cut pattern, which will provide greater flexibility than a two-beam cut pattern, which will provide greater flexibility than a three-beam pattern, and so on.

The terms "approximately," "about," and "substantially" as used herein represent an amount or condition close to the stated amount or condition that still performs a desired function or achieves a desired result. For example, the terms "approximately," "about," and "substantially" may refer to an amount or condition that deviates by less than 10%, or by less than 5%, or by less than 1%, or by less than 0.1%, or by less than 0.01% from a stated amount or condition.

Elements described in relation to any embodiment depicted and/or described herein may be combinable with elements described in relation to any other embodiment depicted and/or described herein. For example, any element described in relation to any of the different cut patterns in FIGS. 4A through 11C may be combinable with any element described in relation to any of the deflectable tip devices of FIGS. 1 through 3.

What is claimed is:

1. An intravascular device, comprising:
   an elongated hollow proximal section;
   an elongated hollow distal section joined to the proximal section and extending distally from the proximal section to form a continuous lumen extending from a proximal end of the device to a distal end of the device; and an inner member extending from the proximal end to the distal end, the inner member being joined to the distal end and being translatable within the lumen in response to applied tension or compression, wherein at least the distal section includes a micro-fabricated cutting pattern that enables deflection of the distal end in response to the application of tension or compression to the inner member, at least a portion of the cutting pattern comprising a spiral pattern configuration with a plurality of bridges connecting adjacent spiral coils of the spiral pattern, the spiral pattern extending to the distal end of the device, wherein the spiral coils of the spiral pattern spiral along the intravascular device at an angle offset from a transverse axis of the intravascular device, wherein at least one bridge of the plurality of bridges extends perpendicular to adjacent spiral coils connected by the at least one bridge, wherein at least two adjacent bridges of the spiral pattern extend angularly offset relative to one another in an axial direction of the intravascular device.

2. The device of claim 1, further comprising a polymeric tip joined to the distal end.

3. The device of claim 2, wherein the polymeric tip is formed from an adhesive material and wherein the inner member is joined to the distal end via the adhesive material.

4. The device of claim 1, wherein the proximal section is a stainless steel tube.

5. The device of claim 1, wherein the distal section is formed from a nickel-titanium alloy.

6. The device of claim 1, wherein the inner member is formed from stainless steel.

7. The device of claim 1, wherein the inner member is a ground stainless steel core that has a wider cross-sectional diameter at a more proximal section and a narrower cross-sectional diameter at a more distal section.

8. An intravascular guidewire device, comprising:
an elongated hollow proximal section;
an elongated hollow distal section joined to the proximal section and extending distally from the proximal section to form a continuous lumen extending from a proximal end of the device to a distal end of the device;
a polymeric tip joined to the distal end of the device; and
an inner member extending from the proximal end to the distal end, the inner member being joined to the distal end via attachment to the polymeric tip, the inner member also being translatable within the lumen in response to applied tension or compression, wherein the distal section includes a micro-fabricated cutting pattern that enables a pre-determined deflection of the distal section in response to the application of tension to the inner member, at least a portion of the cutting pattern comprising a spiral pattern configuration with a plurality of bridges connecting adjacent spiral coils of the spiral pattern, the spiral pattern extending to the distal end of the device, wherein the spiral coils of the spiral pattern spiral along the intravascular device at an angle offset from a transverse axis of the intravascular guidewire device, wherein at least one bridge of the plurality of bridges extends perpendicular to adjacent spiral coils connected by the at least one bridge, wherein at least two adjacent bridges of the spiral pattern extend angularly offset relative to one another in an axial direction of the intravascular guidewire device.

9. The device of claim 8, wherein the polymeric tip is formed from an adhesive material and wherein the inner member is joined to the distal end via the adhesive material.

10. The device of claim 8, wherein the proximal section is a stainless steel tube and the distal section is formed from a nickel-titanium alloy.

11. The device of claim 8, wherein the inner member is formed from stainless steel.

12. The device of claim 8, further comprising a micro catheter, the guidewire device being disposed within the micro catheter such that deflection of the guidewire enables corresponding deflection of the micro catheter.

13. A method of navigating an intravascular device, comprising:
providing an intravascular device as in claim 1;
positioning the intravascular device within a patient's vasculature; and
applying tension to the inner member to cause the distal section of the intravascular device to deflect.

14. The method of claim 13, further comprising positioning the distal end of the guidewire within an aneurysm and applying tension or compression to the inner member to cause the distal end to deflect within the aneurysm.

15. An intravascular device, comprising:
an elongated hollow proximal section;
an elongated hollow distal section joined to the proximal section and extending distally from the proximal section to form a continuous lumen extending from a proximal end of the device to a distal end of the device, the proximal section and distal section being formed from different materials; and
an inner member extending from the proximal end to the distal end, the inner member being joined to the distal end and being translatable within the lumen in response to applied tension or compression, wherein the distal section includes a micro-fabricated cutting pattern that enables a pre-determined deflection of the distal section in response to the application of tension to the inner member, at least a portion of the cutting pattern comprising a spiral pattern configuration with a plurality of bridges connecting adjacent spiral coils of the spiral pattern, the spiral pattern extending to the distal end of the device, wherein the spiral coils of the spiral pattern spiral along the intravascular device at an angle offset from a transverse axis of the intravascular device, wherein at least one bridge of the plurality of bridges extends perpendicular to adjacent spiral coils connected by the at least one bridge, wherein at least two adjacent bridges of the spiral pattern extend angularly offset relative to one another in an axial direction of the intravascular device.

16. The intravascular device of claim 1, wherein at least a portion of the distal section is biased toward a pre-curved shape such that the application of tension to the inner member causes straightening of the distal section.

* * * * *